US009361518B2

(12) United States Patent
Bower et al.

(10) Patent No.: US 9,361,518 B2
(45) Date of Patent: *Jun. 7, 2016

(54) METHODS, SYSTEMS AND COMPUTER PROGRAM PRODUCTS FOR DIAGNOSING CONDITIONS USING UNIQUE CODES GENERATED FROM A MULTIDIMENSIONAL IMAGE OF A SAMPLE

(71) Applicant: Bioptigen, Inc., Morrisville, NC (US)

(72) Inventors: Bradley A. Bower, Hillsborough, NC (US); Eric L. Buckland, Hickory, NC (US)

(73) Assignee: Bioptigen, Inc., Morrisville, NC (US)

( * ) Notice: Subject to any disclaimer, the term of this patent is extended or adjusted under 35 U.S.C. 154(b) by 31 days.

This patent is subject to a terminal disclaimer.

(21) Appl. No.: 14/336,062

(22) Filed: Jul. 21, 2014

(65) Prior Publication Data

US 2014/0341459 A1    Nov. 20, 2014

Related U.S. Application Data

(63) Continuation of application No. 12/953,868, filed on Nov. 24, 2010, now Pat. No. 8,787,623, which is a continuation-in-part of application No. 12/624,937, filed on Nov. 24, 2009, now Pat. No. 8,687,856.

(60) Provisional application No. 61/118,087, filed on Nov. 26, 2008, provisional application No. 61/263,991, filed on Nov. 24, 2009.

(51) Int. Cl.
*G06K 9/00* (2006.01)
*A61B 5/00* (2006.01)
(Continued)

(52) U.S. Cl.
CPC .......... *G06K 9/00604* (2013.01); *A61B 5/0062* (2013.01); *A61B 5/117* (2013.01);
(Continued)

(58) Field of Classification Search
CPC ............ G06K 9/00604; G06K 7/1447; G06K 7/1417; G06K 7/1413; G06K 9/0008; G06K 9/00033; G06K 9/00892; G06T 11/006; A61B 5/0062; A61B 5/117; A61B 5/6821; A61B 5/6826; A61B 5/0068; A61B 5/0066
USPC .......................................... 382/117, 118, 124
See application file for complete search history.

(56) References Cited

U.S. PATENT DOCUMENTS 5,291,560 A   3/1994   Daugman
5,751,835 A   5/1998   Topping et al.
(Continued)

FOREIGN PATENT DOCUMENTS

WO   WO 2008/054396 A1   5/2008
WO   WO 2010/062883 A1   6/2010

OTHER PUBLICATIONS

Chang et al., "Optical coherence tomography used for security and fingerprint-sensing applications," IET Image Process., 2008, vol. 2, No. 1, pp. 48-58.
(Continued)

*Primary Examiner* — John Strege
(74) *Attorney, Agent, or Firm* — Myers Bigel & Sibley

(57) ABSTRACT

Methods of providing a diagnosis using a digital code associated with an image are provided including collecting a multidimensional image, the multidimensional image having at least two dimensions; extracting a two dimensional subset of the multidimensional image; reducing the multidimensional image to a first code that is unique to the multidimensional image based on the extracted two dimensional image; comparing the first unique code associated with the subject to a library of reference codes, each of the reference codes in the library of reference codes being indicative of a class of objects; determining if the subject associated with the first unique code falls into at least one of the classes of objects associated with the reference codes based on a result of the comparison; and formulating a diagnostic decision based on the whether the first unique code associated with the subject falls into at least one of the classes associated with the reference code. Related systems and computer program products are also provided herein.

50 Claims, 32 Drawing Sheets

(51) Int. Cl.
*A61B 5/117* (2016.01)
*G06K 7/14* (2006.01)
*G06T 11/00* (2006.01)

(52) U.S. Cl.
CPC ............ *A61B 5/6821* (2013.01); *A61B 5/6826* (2013.01); *G06K 7/1413* (2013.01); *G06K 7/1417* (2013.01); *G06K 7/1447* (2013.01); *G06K 9/0008* (2013.01); *G06K 9/00033* (2013.01); *G06K 9/00892* (2013.01); *G06T 11/006* (2013.01); *A61B 5/0066* (2013.01); *A61B 5/0068* (2013.01)

(56) References Cited

U.S. PATENT DOCUMENTS

| | | | |
|---|---|---|---|
| 6,219,439 | B1 | 4/2001 | Burger |
| 6,631,199 | B1 | 10/2003 | Topping et al. |
| 6,753,919 | B1 | 6/2004 | Daugman |
| 6,816,605 | B2 | 11/2004 | Rowe et al. |
| 6,907,135 | B2 * | 6/2005 | Gifford ................ G06F 21/32 382/116 |
| 7,545,963 | B2 | 6/2009 | Rowe |
| 2007/0115481 | A1 | 5/2007 | Toth et al. |
| 2007/0160296 | A1 | 7/2007 | Lee et al. |
| 2007/0230754 | A1 | 10/2007 | Jain et al. |
| 2008/0219522 | A1 | 9/2008 | Hook |
| 2009/0163796 | A1 | 6/2009 | Simpson et al. |

OTHER PUBLICATIONS

Cheng et al., "Artificial fingerprint recognition by using optical coherence tomography with autocorrelation analysis," Applied Optics, vol. 45, No. 36, Dec. 20, 2006, pp. 9238-9245.
Daugman and Downing "Epigenetic randomness, complexity and singularity of human iris patterns" (Proc. R. Soc. Lond. B 268, 1737-1740 (2001).
Gamble, et al. "Real-time fingerprint verification system" Applied Optics vol. 31(No. 5): p. 652-655. (Feb. 10, 1992.).
International Preliminary Report on Patentability Corresponding to International Application No. PCT/US2009/065653; Date of Mailing: Jun. 9, 2011; 5 Pages.
International Preliminary Report on Patentability, International Application No. PCT/US2010/057975; May 30, 2012; 8 Pages.
International Search Report and the Written Opinion of the International Searching Authority Corresponding to International Application No. PCT/US2010/057975; Date of Mailing: May 16, 2011; 11 Pages.
Jain et al. "Filterbank-Based Fingerprint Matching" IEEE Transactions on image processing, vol. 9, (No. 5): p. 846-859. (May 2000).
Notification of Transmittal of the International Search Report and the Written Opinion of the International Searching Authority, or the Declaration, PCT/US2009/065653, Apr. 22, 2010, 12 pages.

* cited by examiner

METHODS, SYSTEMS AND COMPUTER PROGRAM PRODUCTS FOR DIAGNOSING CONDITIONS USING UNIQUE CODES GENERATED FROM A MULTIDIMENSIONAL IMAGE OF A SAMPLE

CLAIM OF PRIORITY

The present application is a continuation of U.S. patent application Ser. No. 12/953,868, filed Nov. 24, 2010 (now U.S. Pat. No. 8,787,623), which is a continuation-in-part of U.S. patent application Ser. No. 12/624,937, filed Nov. 24, 2009 (U.S. Pat. No. 8,687,856), which claims priority to U.S. Provisional Application No. 61/118,087, filed Nov. 26, 2008, and claims priority to U.S. Provisional Application No. 61/263,991, filed Nov. 24, 2009, the disclosures of which are hereby incorporated herein by reference as if set forth in their entirety.

FIELD

The present inventive concept relates generally to optical coherence tomography (OCT) and, more particularly, to biometric identification systems that use OCT.

BACKGROUND

The field of biometrics has rapidly evolved in recent years as the need for fast, accurate personal identification has increased. Motivated primarily by national security concerns, law enforcement agencies have expanded well beyond traditional fingerprint identification to, for example, classifiers based on facial topology, vocal patterns, iris structure, and retinal vessel landmarks.

A very good biometric identifier may be one that is measured quickly and easily and is not easily susceptible to cosmetic modification or falsification. This coupled with the work of Daugman and Downing (*Proc. R. Soc. Lond.* B 268, 1737-1740 (2001)) has led to the development of multiple commercially available iris recognition systems.

Using the iris in recognition systems is currently becoming more commonplace. However, iris recognition is a complete paradigm shift from traditional fingerprint recognition systems and, therefore, can be costly to implement and to reconstruct data bases of existing identification files. Furthermore, it may be possible to thwart iris identification using, for example, a patterned contact lens.

U.S. Pat. No. 5,751,835 to Topping et al. discusses the use of the tissue of the fingernail bed as a unique identifier. The tissue under a fingernail is composed of characteristic ridges that form during gestation and are unique to each individual. While the ridges may increase in size as the individual grows, the spacing between the ridges remains consistent over time.

Optical coherence tomography (OCT) is a noninvasive imaging technique that provides microscopic sectioning of biological samples. By measuring singly backscattered light as a function of depth, OCT fills a valuable niche in imaging of tissue structure, providing subsurface imaging with high spatial resolution (~2.0-10.0 µm) in three dimensions and high sensitivity (>110 dB) in vivo with no contact needed between the probe and the tissue.

In biological and biomedical imaging applications, OCT allows for micrometer-scale, non-invasive imaging in transparent, translucent, and/or highly-scattering biological tissues. The depth ranging capability of OCT is generally based on low-coherence interferometry, in which light from a broadband source is split between illuminating the sample of interest and a reference path. The interference pattern of light reflected or backscattered from the sample and light from the reference delay contains information about the location and scattering amplitude of the scatterers in the sample.

In time-domain OCT (TDOCT), this information is typically extracted by scanning the reference path delay and detecting the resulting interferogram pattern as a function of that delay. The envelope of the interferogram pattern thus detected represents a map of the reflectivity of the sample versus depth, generally called an A-scan, with depth resolution given by the coherence length of the source. In OCT systems, multiple A-scans are typically acquired while the sample beam is scanned laterally across the tissue surface, building up a two-dimensional map of reflectivity versus depth and lateral extent typically called a B-scan. The lateral resolution of the B-scan is approximated by the confocal resolving power of the sample arm optical system, which is usually given by the size of the focused optical spot in the tissue. The time-domain approach used in conventional OCT has been successful in supporting biological and medical applications, and numerous in vivo human clinical trials of OCT reported to date have utilized this approach.

An alternate approach to data collection in OCT has been shown to have significant advantages both in reduced system complexity and in increased signal-to-noise ratio (SNR). This approach involves acquiring the interferometric signal generated by mixing sample light with reference light at a fixed group delay in the wavelength or frequency domain and processing the Fourier transform of this spectral interferogram from a wavenumber to a spatial domain. Two distinct methods have been developed which use this Fourier domain OCT (FDOCT) approach. The first, generally termed Spectral-domain or spectrometer-based OCT (SDOCT), uses a broadband light source and achieves spectral discrimination with a dispersive spectrometer in the detector arm. The second, generally termed swept-source OCT (SSOCT) or optical frequency-domain imaging (OFDI), time-encodes wavenumber by rapidly tuning a narrowband source through a broad optical bandwidth. Both of these techniques may allow for a dramatic improvement in SNR of up to 15.0-20.0 dB over time-domain OCT, because they detect all of the backscattered power from the entire relevant sample depth in each measurement interval. This is in contrast to previous-generation time-domain OCT, where destructive interference is typically used to isolate the interferometric signal from only one depth at a time as the reference delay is scanned.

SUMMARY

Some embodiments of the present inventive concept provide methods of providing a diagnosis using a digital code associated with an image, the method including collecting a multidimensional image, the multidimensional image having at least two dimensions; extracting a two dimensional subset of the multidimensional image; reducing the multidimensional image to a first code that is unique to the multidimensional image based on the extracted two dimensional image; comparing the first unique code associated with the subject to a library of reference codes, each of the reference codes in the library of reference codes being indicative of a class of objects; determining if the subject associated with the first unique code falls into at least one of the classes of objects associated with the reference codes based on a result of the comparison; and formulating a diagnostic decision based on the whether the first unique code associated with the subject falls into at least one of the classes associated with the reference code.

In further embodiments of the present inventive concept, determining if the subject associated with the first unique reference code falls into at least one of the classes may further include determining if the subject associated with the first unique reference code has changed classes over time and formulating the diagnostic decision may include formulating the diagnostic decision based on the change of class over time.

In still further embodiments, determining if the subject associated with the first unique code falls into at least one of the classes of objects may include determining that the subject associated with the first unique code falls into at least two of the classes. The method may further include applying additional processing to determine which of the at least two classes more accurately identifies the subject associated with the first unique code.

In some embodiments, the classes associated with the reference code may identify at least one of a physical state and a physical object. The subject may include at least one of a fingernail bed, a fingerprint, an iris, a cornea, any human tissue and physical object.

In further embodiments of the present inventive concept, reducing may further include reducing the two dimensional subset to the first unique code based on a defined set of structural or functional information contained with the image. The method may further include storing the first unique code; and comparing the first unique code to a second unique code to establish a degree of equivalence of the first and second codes.

In still further embodiments of the present inventive concept, the multidimensional image may include at least one of a volumetric image representative of time invariant information in a sample, slowly time-variant information in a sample, or time variant structural or functional information in a sample.

In some embodiments of the present inventive concept, reducing the two dimensional subset to the first unique code may include manipulating the multidimensional data to extract a region of interest; extracting the structural or the functional information using a filter; translating the filtered information into the first unique code representative of the information content contained in the multidimensional data; manipulating the first unique code to be compared to other codes; comparing two or more codes to uniquely identify each code; and assigning a unique identifier to each code.

In further embodiments of the present inventive concept, extracting may include extracting using a filter configured to extract the structural or functional information. The filter may include at least one of a Gabor filter, a complex filter that consists of real and imaginary parts, a complex filter that consists of a spatial frequency component and a Gaussian window component and a complex filter that has at least three unique degrees of freedom including amplitude, at least one spatial frequency, and at least one Gaussian window standard deviation.

In still further embodiments of the present inventive concept, the filter may be configured to operate on a two dimensional subset using at least one of a convolution in the native domain or a multiplication of the Fourier Transforms of the filter and two dimensional subset and multiple filter scales in which one or more filter degrees of freedom are changed before combination with the image subset.

In some embodiments of the present inventive concept, the unique code may be obtained from complex data comprising at least one of a complex representation of the filter combined with the image subset in which the complex result is treated as a vector in the complex plane and a method in which the angle of the vector in the complex plane is determined and a code representative of the quadrant in the complex plane containing the vector angle is generated.

In further embodiments of the present inventive concept, the unique code may be binary such that each pixel of information is represented by one of two states.

In still further embodiments of the present inventive concept, the unique code may have a base greater than 2.

In still further embodiments of the present inventive concept, the unique code may be represented as a one or two dimensional barcode configured to be read by a generic commercial barcode reading technology.

In some embodiments of the present inventive concept, comparing may include comparing two or more unique codes using cross-correlation or other relational comparison.

In further embodiments of the present inventive concept, the relational comparison may be an XOR operation. The comparison result may be applied to find a Hamming distance. The Hamming distance may be used to validate a strength of the comparison against a database of other codes.

In still further embodiments of the present inventive concept, the extracting, translating, manipulating, comparing and assigning steps may be repeated to construct a database of codes. A unique identifier threshold may be defined based on sensitivity analysis of the codes in the database. The method may further include determining if a calculated code is unique or present in the database by comparing the unique identifier threshold to the Hamming distance between the calculated code and the codes in the database.

In some embodiments of the present inventive concept, the filter may include any image processing system in which information content is emphasized or extracted from a depth-dependent image.

In further embodiments of the present inventive concept, the filter may be at least one of a speckle tracking algorithm and a texture-based image analysis algorithm.

Still further embodiments of the present inventive concept provide methods of providing a diagnosis based on a digital code in an optical coherence tomography imaging system, the method including acquiring interferometric cross-correlation data representative of multidimensional information unique to a sample, the multidimensional information including one, two, or three spatial dimensions plus zero, one or two time dimensions; processing the multidimensional interferometric cross-correlation data into one or more images processed to represent one or more of time invariant information about the sample, slowly time variant information about the sample, or time variant structural or functional information about the sample; and selecting a subset of the multidimensional data; reducing the selected subset of data to a two dimensional subset of data; performing one or more spatial or temporal frequency transforms of the two dimensional subsets to derive a unique representation of the sample; reducing the transform into a unique digital code associated with the sample; comparing the unique digital code associated with the sample to a library of reference codes, each of the reference codes in the library of reference codes being indicative of a class of objects; determining if the sample associated with the unique digital code falls into at least one of the classes of objects associated with the reference codes based on a result of the comparison; and formulating a diagnostic decision based on the whether the unique digital code associated with the sample falls into at least one of the classes associated with the reference code.

In some embodiments of the present inventive concept the optical coherence tomography system may include an optical source; an optical splitter configured to separate a reference optical signal from a sample optical signal; and an optical detector configured to detect an interferometric cross-correlation between the reference optical signal and the sample optical signal.

In further embodiments of the present inventive concept, the unique digital code may include a first unique digital code. The method may further include storing the digital code; comparing the first unique digital code to a second unique digital code of the sample acquired from a second position within the sample, of the same sample acquired at a different time and/or of a different sample; and establishing a degree of equivalence between the first and second unique digital codes.

Still further embodiments of the present inventive concept provide methods of providing a diagnosis using a digital code using a Fourier domain optical coherence tomography imaging system, the method including acquiring frequency-dependent interferometric cross-correlation data representative of multidimensional information unique to a sample, the multidimensional information including zero or one frequency dimensions, one, two, or three spatial dimensions and zero, one, or two time dimensions; processing the multidimensional interferometric cross-correlation data into one or more images processed to represent one or more of time invariant information about the sample, slowly time variant information about the sample, or time variant structural or functional information about the sample; selecting a subset of the multidimensional data; reducing the subset of data to a two dimensional subset of data; performing one or more spatial or temporal frequency transforms of the two dimensional subsets to derive a unique representation of the sample; reducing the transform into a unique digital code that provides a unique signature of the multidimensional data; comparing the unique digital code associated with the sample to a library of reference codes, each of the reference codes in the library of reference codes being indicative of a class of objects; determining if the sample associated with the unique digital code falls into at least one of the classes of objects associated with the reference codes based on a result of the comparison; and formulating a diagnostic decision based on the whether the unique digital code associated with the sample falls into at least one of the classes associated with the reference code.

In some embodiments of the present inventive concept, the Fourier domain optical coherence tomography imaging system may include an optical source; an optical splitter configured to separate a reference optical signal from a sample optical signal; and an optical detector configured to detect a frequency-dependent interferometric cross-correlation between the reference signal and the sample signal.

In further embodiments of the present inventive concept, the unique digital code may be a first unique digital code and the method may further include storing the unique digital code; comparing the unique digital code to a second unique digital code of the same sample acquired from a separate position within the sample, of the sample acquired at a separate time, of a different sample; and establishing a degree of equivalence between the first and second unique digital codes.

In still further embodiments of the present inventive concept, processing of frequency-dependent interferometric cross-correlation data may include obtaining a Fourier transformation of the frequency-dependent dimension to provide a spatial dimension.

In some embodiments of the present inventive concept, the image may be a volumetric image of a fingernail of a subject, the volumetric image may include a series of one-dimensional lines that provide information on scattering from the fingernail and fingernail bed as a function of depth, a series of lines optically contiguous may be arrayed in a two-dimensional frame that represents a cross section of the fingernail perpendicular to an axis of the finger, and the method may further include acquiring a series of frames to produce a volume.

In further embodiments of the present inventive concept, the method may further include segmenting a nailbed from within the volumetric image of the fingernail using an automated or manual segmentation technique; and averaging one or more frames in order to produce an average-valued image of multiple cross-sectional locations of the nailbed or to improve the signal-to-noise ratio of the nailbed image along one cross-section.

In still further embodiments of the present inventive concept, the method may further include processing a digital code from the cross-sectional image of segmented nailbed region of at least one frame. Processing the multidimensional interferometric cross-correlation data may include processing an intensity projection from two or more frames of the segmented nailbed, the method further comprising processing a digital code from the intensity projection.

In some embodiments of the present inventive concept, the image may be a volumetric image of an iris of an eye of a subject, the volumetric image may include a series of one-dimensional lines that provide information on scattering from the iris as a function of depth, a series of lines optically contiguous may be arrayed in a two-dimensional frame that represents a cross section of the iris perpendicular to an axis of the eye, and the method may further include acquiring a series of frames to produce a volume.

In further embodiments of the present inventive concept, the method may further include constructing the volumetric image from a series of concentric circular scans approximately centered on a pupil of the eye.

In still further embodiments of the present inventive concept, the method may further include segmenting one or more layers of the iris from within the volumetric image of the iris using an automated or manual segmentation technique; and averaging one or more frames in order to produce an average-valued image of multiple cross-sectional locations of the iris or to improve the signal-to-noise ratio of the iris image at cross section.

In some embodiments of the present inventive concept, the method further includes processing a digital code from the cross-sectional image of segmented iris region of at least one frame.

In further embodiments of the present inventive concept, the method may further include processing an intensity projection from two or more frames of the segmented iris; and processing a digital code from the intensity projection.

Although embodiments of the present inventive concept are primarily discussed above with respect to method embodiments, systems and computer program products are also discussed herein.

DETAILED DESCRIPTION

Figure 1:
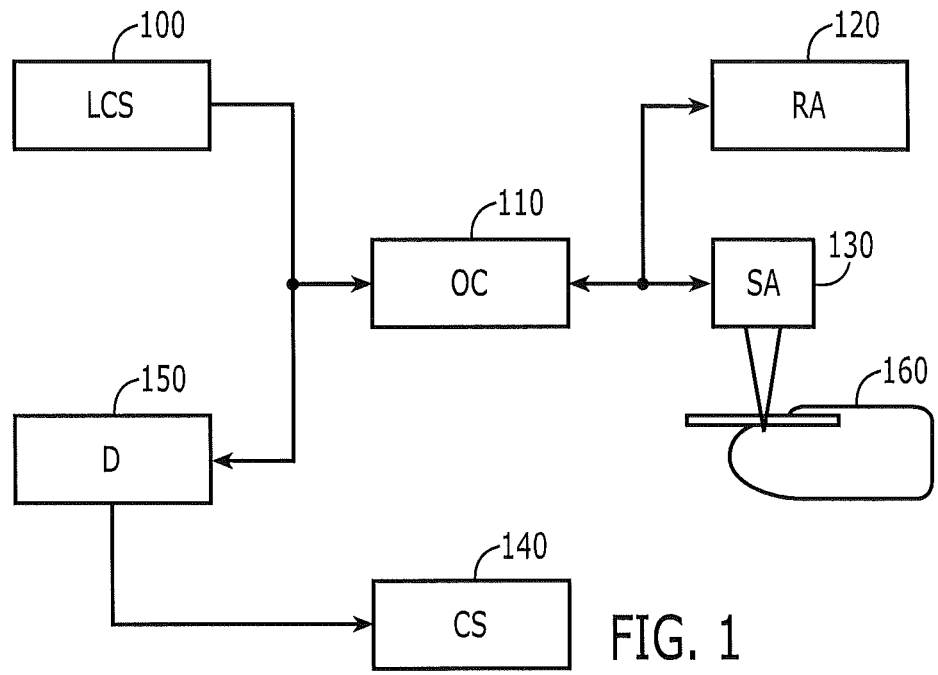
FIG. 1 is a block diagram illustrating a raster scanning FDOCT system for fingernail bed imaging according to some embodiments of the present inventive concept.

The inventive concept now will be described more fully hereinafter with reference to the accompanying drawings, in which illustrative embodiments of the inventive concept are shown. This inventive concept may, however, be embodied in many different forms and should not be construed as limited to the embodiments set forth herein; rather, these embodiments are provided so that this disclosure will be thorough and complete, and will fully convey the scope of the inventive concept to those skilled in the art. Like numbers refer to like elements throughout. As used herein, the term "and/or" includes any and all combinations of one or more of the associated listed items.

The terminology used herein is for the purpose of describing particular embodiments only and is not intended to be limiting of the inventive concept. As used herein, the singular forms "a", "an" and "the" are intended to include the plural forms as well, unless the context clearly indicates otherwise. It will be further understood that the terms "comprises" and/or "comprising," when used in this specification, specify the presence of stated features, integers, steps, operations, elements, and/or components, but do not preclude the presence or addition of one or more other features, integers, steps, operations, elements, components, and/or groups thereof.

Unless otherwise defined, all terms (including technical and scientific terms) used herein have the same meaning as commonly understood by one of ordinary skill in the art to which this inventive concept belongs. It will be further understood that terms, such as those defined in commonly used dictionaries, should be interpreted as having a meaning that is consistent with their meaning in the context of the relevant art and this specification and will not be interpreted in an idealized or overly formal sense unless expressly so defined herein.

As used herein, "time invariant" refers to a property that does not change over a time period of interest. For example, the structure of the iris in a normal healthy individual. "Slowly time variant" refers to a property that does not vary measurably within one measurement acquisition, but may change between measurements. For example, the course of blood vessels in a patient with diabetic retinopathy. "Time variant" refers to a property that is measurably changing during the course of one measurement event. For example, the pulsatility of an ocular artery. "Structural information" refers to morphological information arising from a combination of scattering and absorption in a tissue, without reference to, for example, spectroscopic or phase information. "Functional information" refers to information arising out of a physiological or metabolic condition of a sample, for example, wavelength dependent absorption or scattering (spectroscopic), birefringence (polarization sensitivity), or phase or flow information (e.g. Doppler).

"En face" refers to a plane parallel to the plane of the surface of the tissue being imaged. "Intensity projection" refers to one of any processing techniques known by those having skill in the art or anticipated to create an en face view of a volumetric image set. It will be further understood that as used herein transformation of an optical information set from frequency to time is equivalent to a transformation between frequency and space.

As is understood by those having skill in the art, a biometric identification system typically uses a unique personal attribute that can be measured with high sensitivity and specificity. To obtain the best results, this attribute should be an attribute that cannot be easily modified or falsified cosmetically and yet is quickly and easily measured via non-invasive means. A secondary measurement may be acquired to re-enforce the primary measurement or to correlate with traditional measurement systems. For example, the primary attribute may be a human fingernail bed as processed in an FDOCT imaging system, and the secondary attribute may be an image of the fingerprint. The image of the secondary attribute may be an analog or digital photograph, or it may be an en face image derived from an OCT image set. Although embodiments of the present inventive concept are discussed herein with respect to the human fingernail bed, embodiments of the present inventive concept are not limited to this attribute. For example, the iris may also be used as the attribute without departing from the scope of the present inventive concept. The attribute in accordance with some embodiments of the present inventive concept may be quickly and easily measured using Fourier Domain Optical Coherence Tomography (FDOCT) as will be discussed further herein with respect to FIGS. 1 through 23.

In particular, some embodiments of the present inventive concept depth-section the tissue below the nail and generate unique 2-D topographical maps of depth as a function of lateral position at each spatial location across the nail using optical coherence tomography (OCT).

In particular, some embodiments of the present inventive concept discuss a novel, non-invasive optical biometric classifier. Some embodiments discussed herein utilize optical coherence tomography to resolve tissue microstructure in the human fingernail bed. However, it will be understood that the concepts can be applied using other depth-resolved imaging techniques, such as scanning confocal microscopy, without departing from the scope of the present inventive concept.

In some embodiments of the present inventive concept, an FDOCT system is used to obtain a volumetric image of the target tissue. Light from an optical source is directed via an optical splitter through a reference and sample arm path, reflected off of reference reflector in the reference arm and backscattered from the tissue in the sample arm. The reference and sample signals are mixed in an optical coupler and the mixed light is directed to an optical detector. Interferometric cross-correlation terms are sampled in the frequency domain and processed using methods known to those skilled in the art to produce an array of depth-dependent data at one spatially unique location on the sample; this array of depth resolved data is known as an A-scan.

An array of A-Scans acquired as a beam scans a direction across the sample and forms a two-dimensional cross-sectional image of a slice of the tissue; this cross-sectional image is known as a B-Scan. A B-Scan may be useful for obtaining time-invariant or time slowly-variant images of a sample. A collection of multiple B-Scans acquired across the sample defines an OCT volume.

In some embodiments of the present inventive concept, an array of A-Scans acquired as a function of time at one spatial location is known as an M-Scan. An M-scan may be useful for obtaining time-variant images of a sample.

In some embodiments of the present inventive concept, the OCT image may be obtained by scanning the sample light across the sample and at each spatially unique point to acquire a spectral interferogram whose intensity is a function of the depth-dependent back-scattering intensity of the sample.

In some embodiments of the present inventive concept, full-field OCT imaging may be provided using a large collimated spot on the sample and a narrow instantaneous linewidth from the source. This can be accomplished using, for example, a swept laser source or a superluminescent diode with a tunable filter. In these embodiments of the present inventive concept, spectral images may be acquired in a plane parallel to the surface of the tissue, which are then processed using FDOCT processing techniques known to those having skill in the art.

Projections through volumetric data sets can be used to decrease the dimensionality of the image data and provide a unique representation of the two dimensional (2D) structure appropriate to the attribute of interest. A projection created by processing the image intensity along the depth axis of a three dimensional (3D) volume produces an en face image of the volumetric data. This en face image can then be correlated with other OCT-generated en face images or photographs acquired through other imaging modalities, for example, standard flash photography, to track motion between subsequent volumes or to align the structure in the volume data for longitudinal analysis.

In some embodiments, projecting through the data may be accomplished using the average intensity projection, also known as the volume intensity projection, in which the signal intensity along each A-scan is averaged, collapsing each depth line to a single point representative of the average intensity along each depth line. The 2D en face image is composed of all points generated from the processing above.

In further embodiments of the present inventive concept, generating an intensity projection is the maximum intensity projection, in which the maximum value of each A-Scan is calculated and stored, collapsing each depth line to a single point containing the maximum intensity value along each depth line. The 2D en face image is composed of all points generated from the processing above.

In some embodiments of the present inventive concept, generating an intensity projection is a histogram-based method in which the histogram of the intensity of each A-Scan is calculated and the maximum value of the histogram is stored, collapsing each depth line to a single point containing the maximum value of the histogram for each depth line. The 2D en face image is composed of all points generated from the processing above.

In some embodiments of the present inventive concept, generating an intensity projection is a histogram-based method in which the histogram of the intensity of each A-Scan is calculated and the centroid or center of mass of the histogram is stored, collapsing each depth line to a single point containing the center of mass of the histogram for each depth line. The 2D en face image is composed of all points generated from the processing above.

Although particular methods for calculating the intensity projection have been discussed above, embodiments of the present inventive concept are not limited to this configuration. For example, methods may be used to calculate the intensity projection based on standard algebraic operations. The intensity projections stated may be used along axes not parallel to the plane of the tissue surface to create projections through the 3D volume that are not en face, but do create an alternate 2D representation of the 3D volume data.

Referring first to FIG. 1, a block diagram illustrating a raster scanning FDOCT system for imaging in accordance with some embodiments of the present inventive concept will be discussed. As illustrated in FIG. 1, the FDOCT system includes a low-coherence source (LCS) 100, an optical coupler (OC) 110, a reference arm (RA) 120, a sample arm (SA) 130, a computer system (CS) 140, a detector (D) 150 and a sample 160. The LCS 100 may be, for example, a broadband superluminescent diode having a center wavelength in the near-infrared (IR) or IR range with sufficient bandwidth to have less than about 20 µm axial and lateral resolution in tissue. Light from the diode is passed through the optical coupler 110 to a fixed reference arm 120 discusses below with respect to FIGS. 9 and 21 and the sample arm 130 that raster scans the beam across the sample 160. Reference and sample arm light are mixed in the optical coupler 110 and detected in parallel by the detector 150 using a one dimensional (1D) array detector, such as the SDOCT detector 151 of FIG. 10.

In some embodiments, a tunable, or swept source may be used in place of the LCS 100, and the spectral interferogram may be collected serially with one or more point detectors. Once the spectral interferogram is acquired and resampled into a wavenumber array, the Fourier processing algorithms for the SDOCT and the SSOCT images are similar.

Referring again to FIG. 1, the computer system 140 may be used to process and analyze the data. 2D slice scans or 3D volume scans may be used to acquire depth slices through the fingernail bed. For many embodiments of the present inventive concept discussed herein, multiple A-Scan one dimensional (1D) depth lines or B-Scan 2D depth slices may be acquired and averaged as a function of time to improve the signal-to-noise ratio of the acquired data.

Figure 2:
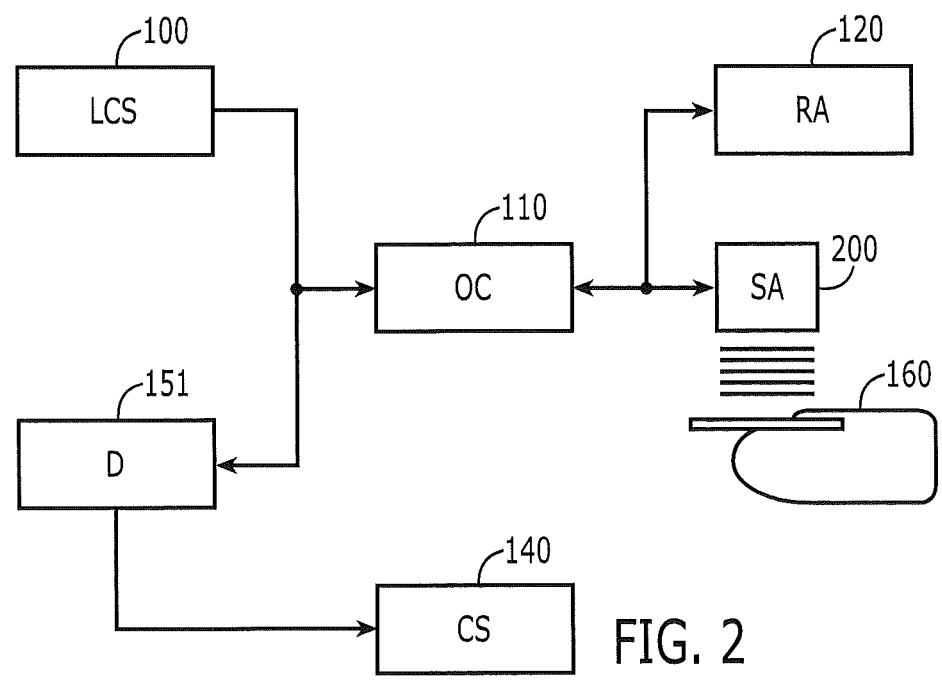
FIG. 2 is a block diagram of a full-field FDOCT system for fingernail bed imaging according to some embodiments of the present inventive concept.

Referring now to FIG. 2, a block diagram of a full-field FDOCT system for imaging in accordance with some embodiments of the present inventive concept will be discussed. Like elements refer to like reference numerals throughout the specification. Accordingly, the LCS 100, the optical coupler 110, the reference arm 120, the computer system 140, and the sample 160 are similar to those discussed above with respect to FIG. 1. However, in embodiments illustrated in FIG. 2, a scanning fiber Fabry-Perot (FFP) filter is used to rapidly sweep through the wavelength output range. Light from the filter is passed through an optical coupler 110 to a fixed reference arm 120 and a sample arm 200 that expands and collimates the beam incident on a large area of the sample. Reference and sample arm light are mixed in the optical coupler 110 and detected using 2-D, full-field array detector 151, such as the FFOCT detector 153 of FIG. 10.

Figure 3:
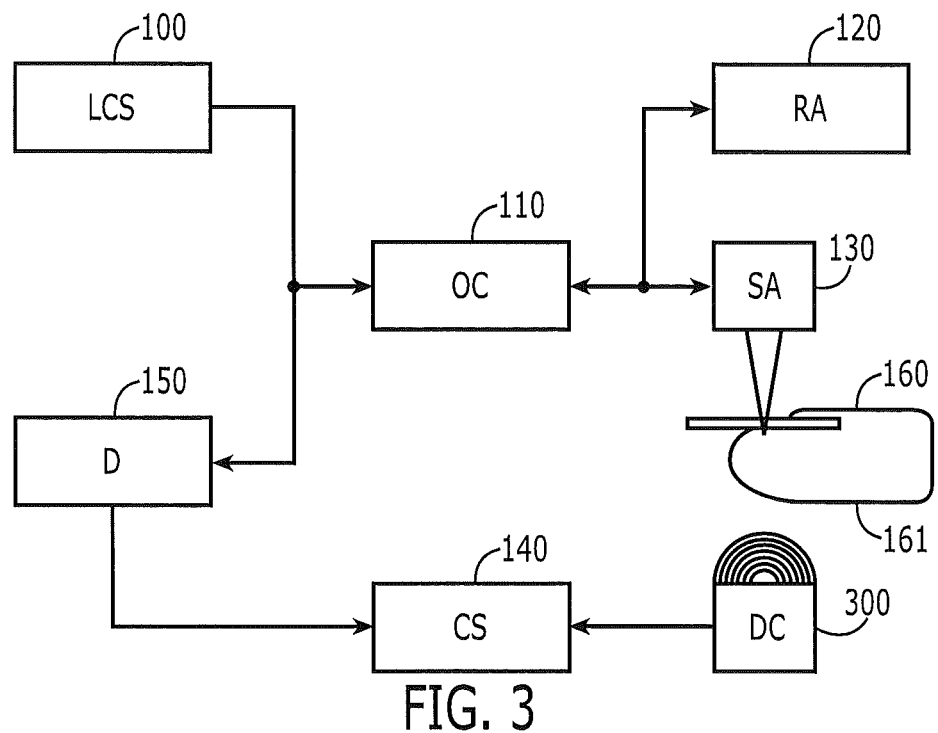
FIG. 3 is a block diagram of a raster scanning FDOCT system including a digital capture system for fingernail bed imaging according to some embodiments of the present inventive concept.

Referring now to FIG. 3, a block diagram of a raster scanning FDOCT system with a digital image capture capability according to some embodiments of the present inventive concept will be discussed. As discussed above, like elements refer to like elements throughout. Accordingly the LCS 100, the optical coupler 110, the reference arm 120, the sample arm 130, the computer system 140, the detector 150 and the sample 160 are similar to those discussed above with respect to FIG. 1. However, as illustrated in FIG. 3, the system of FIG. 3 includes a digital capture system 300. The digital capture system 300 may be, for example, a high speed video camera or a high resolution still camera. The digital capture system 300 illustrated in FIG. 3 may be used to capture the fingerprint 161 of the sample while the FDOCT system captures the fingernail bed data. The digitally captured image may be used in standard digital fingerprint identification databases to append the unique code to existing identification information.

Figure 4:
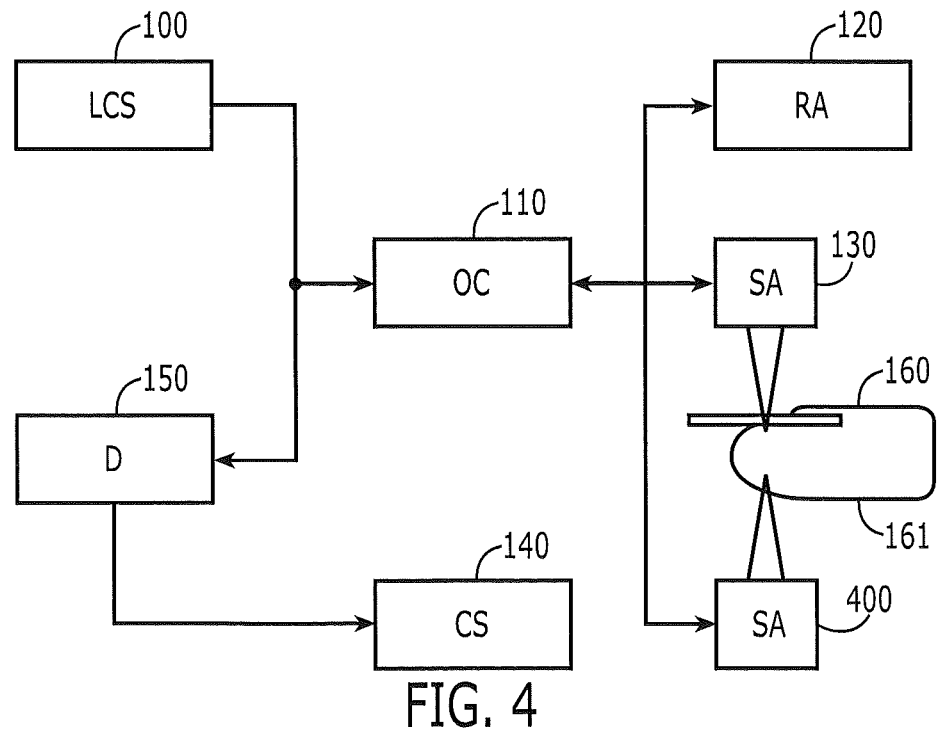
FIG. 4 is a block diagram of a dual, raster scanning FDOCT system for combined fingernail bed and fingerprint imaging according to some embodiments of the present inventive concept.

Referring now to FIG. 4, a block diagram of a dual raster scanning FDOCT system according to some embodiments of the present inventive concept will be discussed. As discussed above, like elements refer to like elements throughout. Accordingly the LCS 100, the optical coupler 110, the reference arm 120, the computer system 140, the detector 150 and the sample 160 are similar to those discussed above with respect to FIG. 1. However, the FDOCT system of FIG. 4 includes two samples arms 130 and 400. The FDOCT sample arm 400 is used to raster scan the fingerprint 161 at the same time as the fingernail bed 160 is raster scanned by 130. The volumetric FDOCT data may be processed to retrieve an en face image of the fingerprint, which in turn may be used in standard digital fingerprint identification databases to append the unique code to existing identification information. Embodiments of the present inventive concept are not limited to the configuration of FIG. 4. For example, the system may be implemented using multiple reference arm topologies illustrated in FIG. 9.

Figure 9:
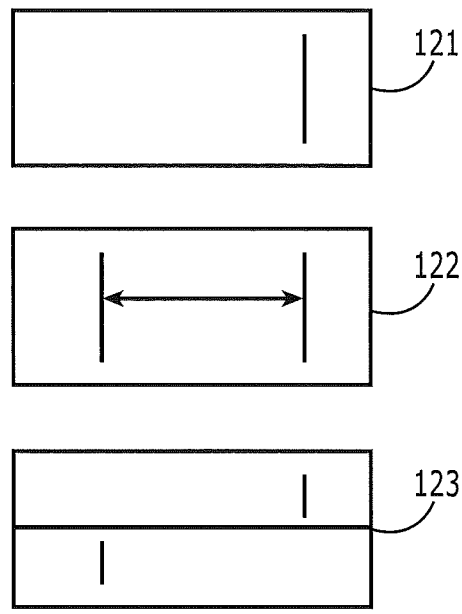
FIG. 9 is a block diagram illustrating representative reference arm configurations according to some embodiments of the present inventive concept.
Figure 10:
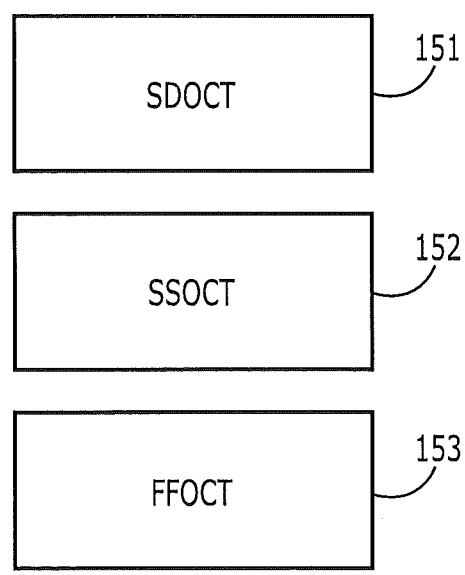
FIG. 10 is a block diagram illustrating representative FDOCT detection methods according to some embodiments of the present inventive concept.

Referring now to FIG. 9, various reference arm configurations in accordance with some embodiments of the present inventive concept will be discussed. As illustrated in FIG. 9, element 121 is a fixed path length reference arm. As further illustrated in FIG. 9, element 122 is a switched reference arm that alternates between two unique reference arm positions, allowing serial acquisition of the signal from the two unique sample arms. Still further illustrates in FIG. 9, element 123 is a static reference arm in which the reference arm light is split between two unique paths matched to the sample arm paths. This implementation typically requires depth multiplexing at the detector and as such a detection method with sufficient depth range to accommodate the two sample arm images must be used.

Figure 5:
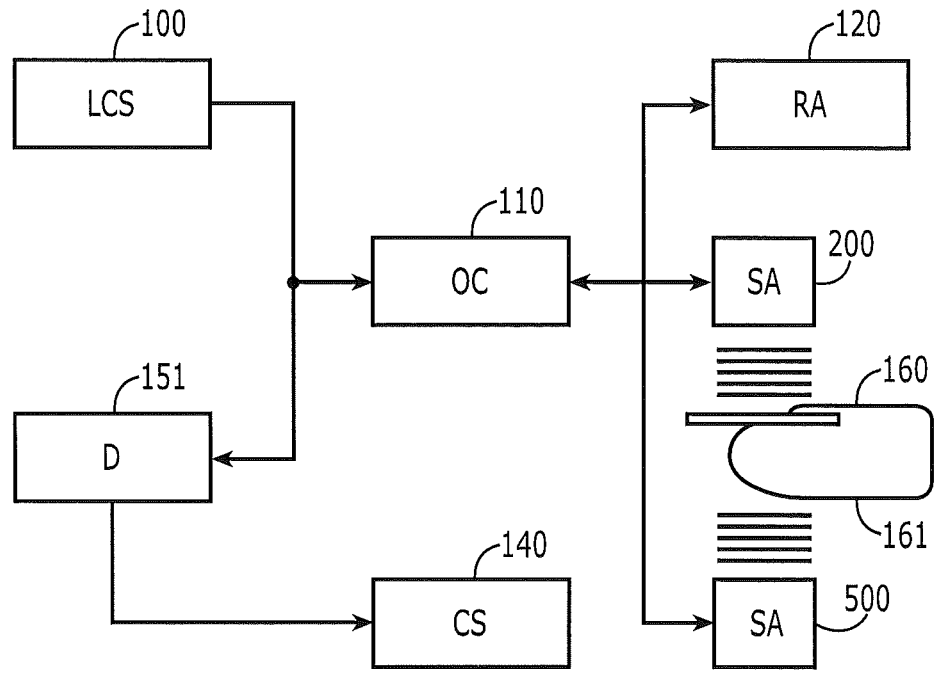
FIG. 5 is a block diagram of a dual, full-field FDOCT system for combined fingernail bed and fingerprint imaging according to some embodiments of the present inventive concept.

Referring now to FIG. 5, a block diagram of a dual, full-field FDOCT system for combined fingernail bed and fingerprint imaging according to some embodiments of the present inventive concept will be discussed. As discussed above, like reference numerals refer to like elements throughout. Accordingly, the LCS 100, the optical coupler 110, the reference arm 120, the sample arm 200, the computer system 140, the detector 151 and the sample 160 are similar to those discussed above with respect to FIG. 2. However, embodiments illustrated in FIG. 5 include a second full-field sample arm 500, which uses a switched reference arm 122 discussed above with respect to FIG. 9.

Figure 6:
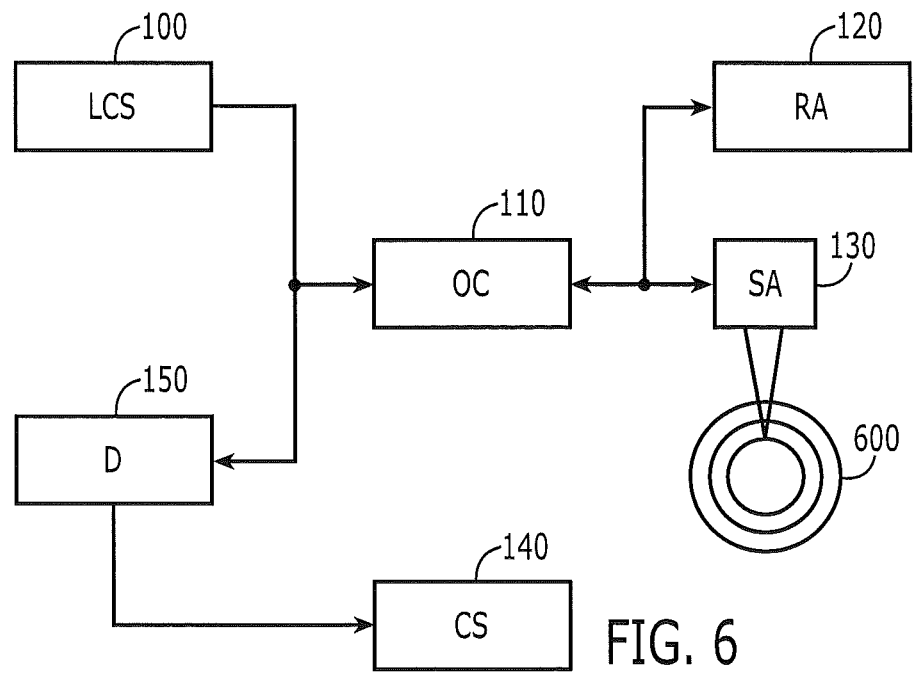
FIG. 6 is a block diagram of a raster scanning FDOCT system for iris imaging according to some embodiments of the present inventive concept.

Referring now to FIG. 6, a block diagram of a raster scanning FDOCT system for iris imaging according to some embodiments of the present inventive concept will be discussed. As discussed above, like elements refer to like elements throughout. Accordingly the LCS 100, the optical coupler 110, the reference arm 120, the sample arm 130, the computer system 140, and the detector 150 are similar to those discussed above with respect to FIG. 1. However, as illustrated in FIG. 6, the system of FIG. 6 is used to image an iris 600. Rectangular volume scans or circular scans acquired through the iris may be used to capture depth slices through the iris according to some embodiments of the present inventive concept as will be discussed further below.

Figure 7:
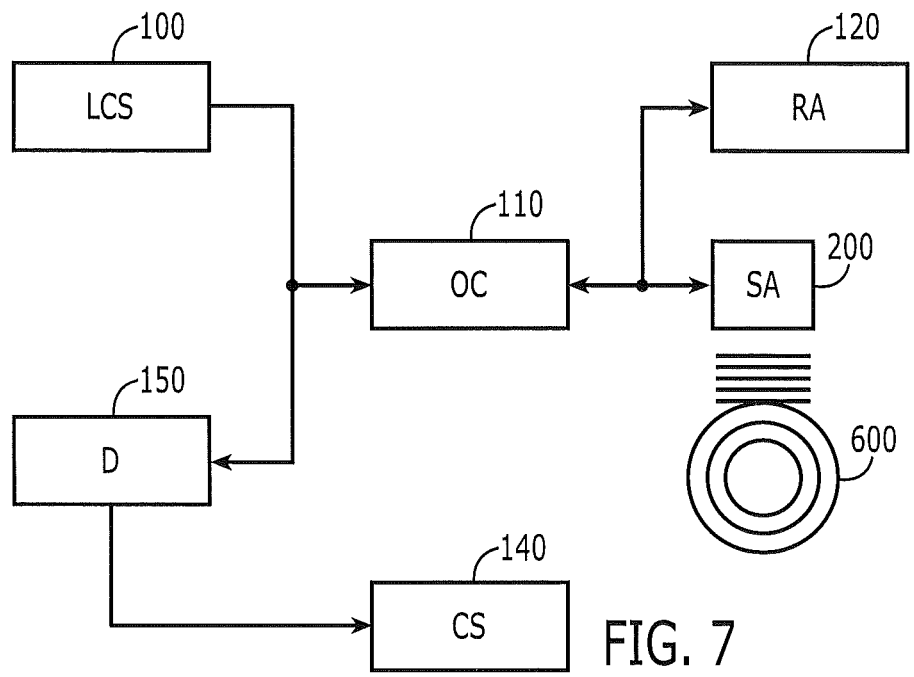
FIG. 7 is a block diagram of a full-field FDOCT system for iris imaging according to some embodiments of the present inventive concept.

Referring now to FIG. 7, a block diagram of a full-field FDOCT system for iris imaging according to some embodiments of the present inventive concept will be discussed. As discussed above, like reference numerals refer to like elements throughout. Accordingly, the LCS 100, the optical coupler 110, the reference arm 120, the sample arm 200, the computer system 140 and the detector 150 are similar to those discussed above with respect to FIG. 2. However, as illustrated in FIG. 7, the system of FIG. 7 is used to image an iris 600.

Figure 8:
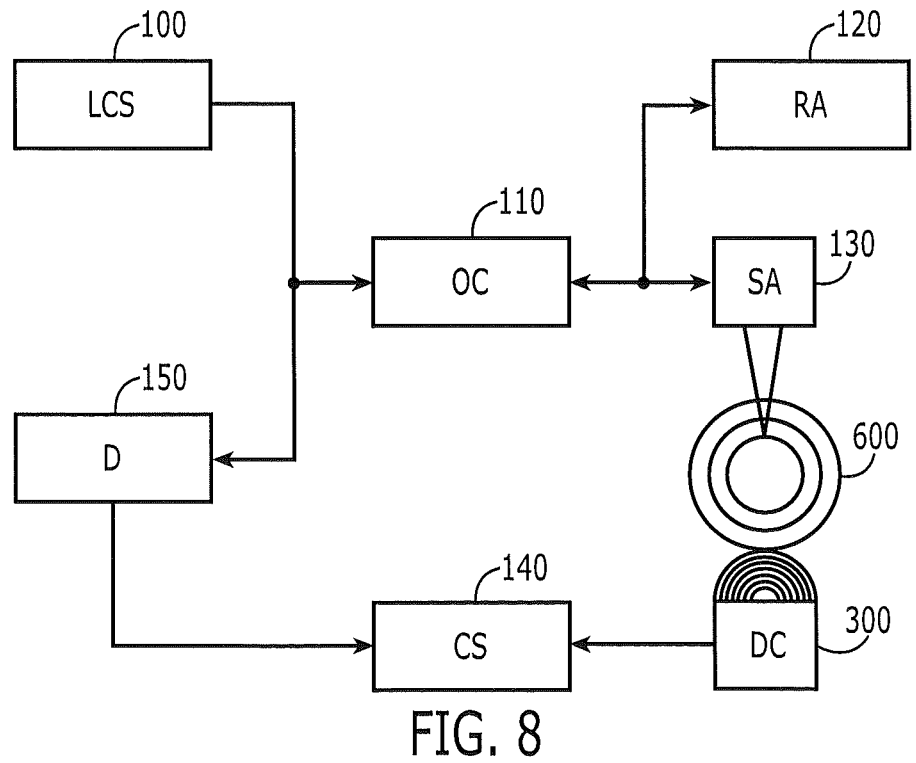
FIG. 8 is a block diagram of a raster scanning FDOCT system with combined digital capture system for iris imaging according to some embodiments of the present inventive concept.

Referring to FIG. 8, a block diagram of a raster scanning FDOCT system with combined digital capture system according to some embodiments of the present inventive concept will be discussed. As discussed above, like elements refer to like elements throughout. Accordingly the LCS 100, the optical coupler 110, the reference arm 120, the sample arm 130, the computer system 140, the detector 150 and the digital capture system 300 are similar to those discussed above with respect to FIG. 3. However, as illustrated in FIG. 8, the system of FIG. 8 is used to acquire both FDOCT and digital capture 300 images of the iris 600.

Figure 11:
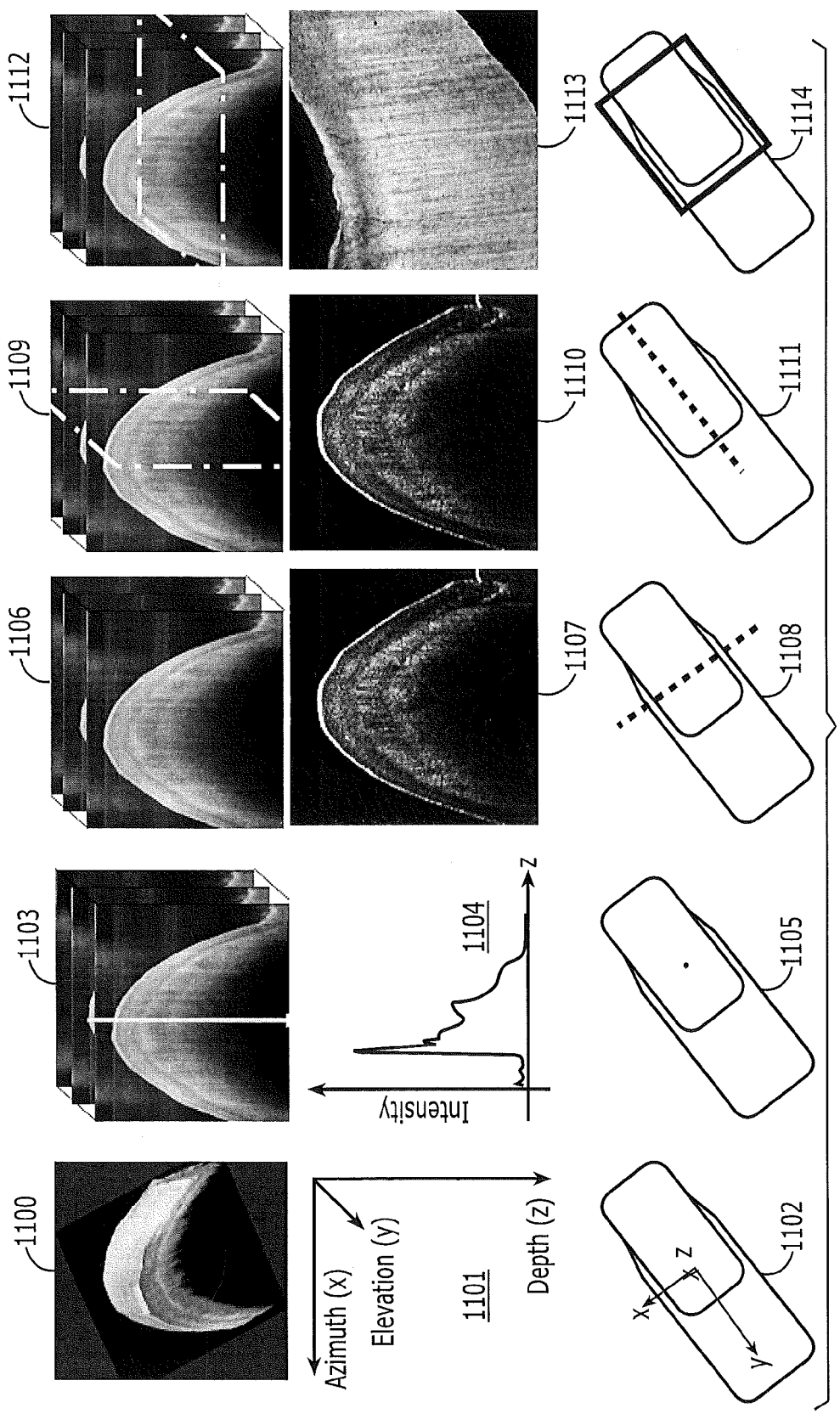
FIG. 11 are images and graphs illustrating slice planes through a 3D volume in the fingernail bed according to some embodiments of the inventive concept.

Referring now to FIG. 11, images and graphs illustrating slice planes through a 3D volume in the fingernail bed according to some embodiments of the inventive concept will be discussed. Some embodiments of the present inventive concept involve the generation of a unique code from a 2-dimensional slice 1107 through a 3-dimensional volume 1100 acquired at the fingernail bed. The orientation axes 1101 and corresponding fingernail orientation 1102 are illustrated in FIG. 11. The traditional B-Scan consists of spatially unique locations along the azimuth dimension 1101 with a volume consisting of multiple B-Scans at spatially unique planes along the elevation dimension. A single depth line 1103 (A-Scan) provides an intensity profile 1104 at a single, spatially unique scan position 1105. Transverse B-Scan slices 1106 provide images as a function of azimuth and depth 1107 through the nailbed 1108. Sagittal slices through the structure 1109 provide similar B-Scan images 1110 through the nailbed 1111. Once an FDOCT volume has been acquired, coronal slices 1112 and corresponding C-Scan images 1113 can be reconstructed for the nailbed 1114. In some embodiments of the present inventive concept, a raster scan orthogonal to the banded structure in the fingernail bed may be used. By acquiring multiple scans orthogonal to the bands in the bed at different positions across the nail, a volume of data 1100 is generated. Generating a projection along the depth axis returns a volume intensity projection. Some embodiments of the present inventive concept improve upon conventional methods by the addition of the depth dimension, which permits multiple methods of analysis.

Figure 12B:
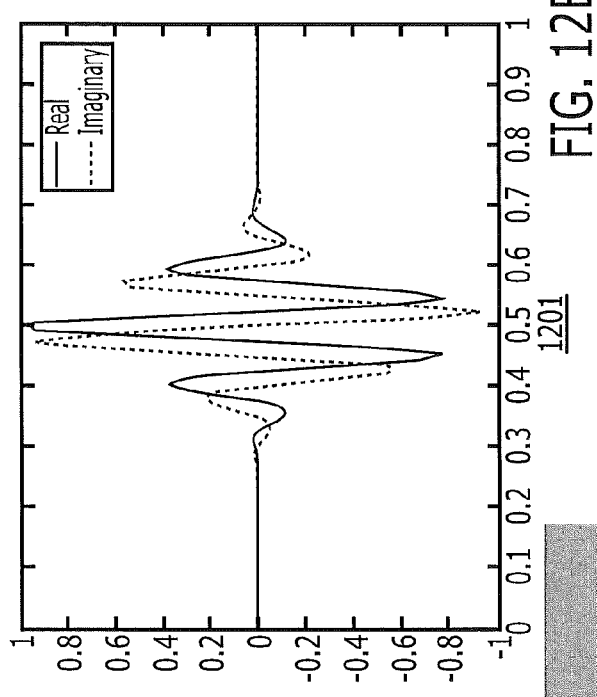
FIGS. 12A, B and C are graphs and images illustrating generation and evolution of the Gabor filter according to some embodiments of the present inventive concept.
Figure 12C:
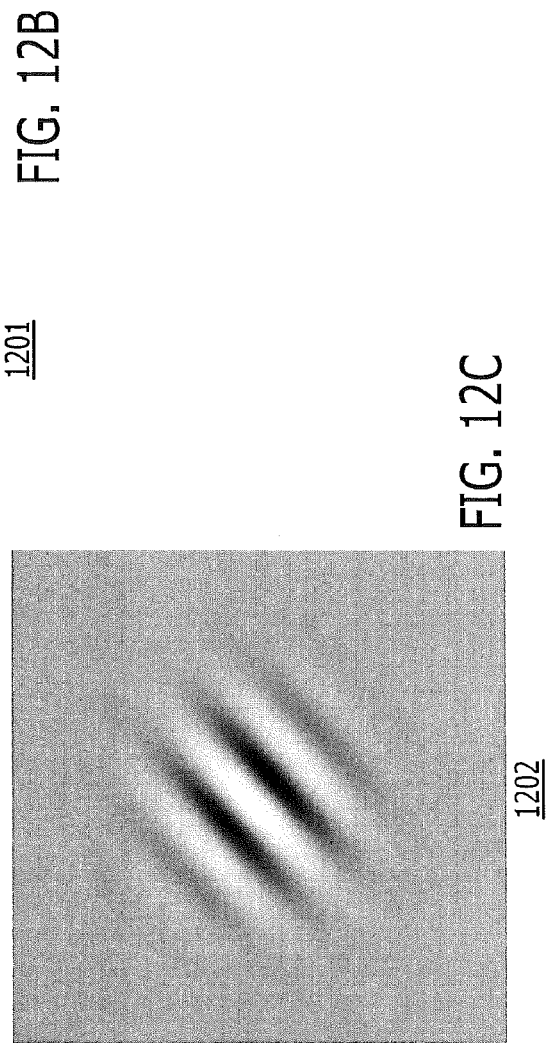
Figure 12A:
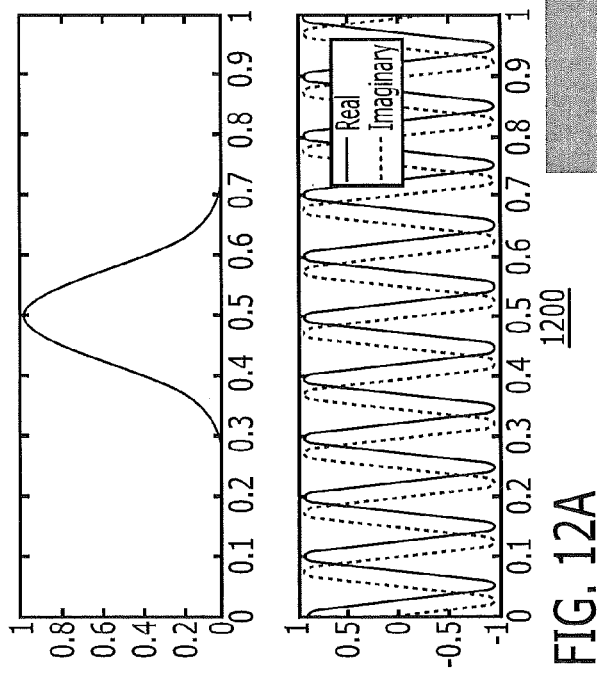

Referring now to FIGS. 12A, B and C, graphs and images illustrating generation and evolution of the Gabor filter according to some embodiments of the present inventive concept will be discussed. Some embodiments of the present inventive concept use the Gabor wavelet as the filtering function. Daugman proposes the use of the Gabor wavelet to analyze the localized spatial frequency content of the warped iris image. Similar processing may be applied to the banded structure of the fingernail bed. The 1-D Gabor filter is composed of a complex exponential windowed by a Gaussian 1200:

$$f(A, u, x, \sigma_x) = \exp(-2\pi i u x) * \exp\left(\frac{-(x-x_0)^2}{\sigma_x^2}\right) \quad \text{[Eqn. 1]}$$

where $f(A,u,x,\sigma_x)$ is the filtering function, A is the amplitude of the function, i is the imaginary variable, u is the spatial frequency, x is the space variable, $x_0$ is some offset in space that defines the center of the Gaussian envelope, and $\sigma_x$ is the standard deviation that defines the width of the Gaussian envelope. The real and imaginary parts 1201 are sinusoids windowed by a Gaussian function.

The 2-dimensional extension of Eqn. 1 becomes Eqn. 2:

$$f(A, u, v, x, y, \sigma_x, \sigma_y) = \\ A\exp\left(-2\pi i(ux+vy)^*\exp\left(\frac{-(x-x_0)^2}{\sigma_x^2}\right) * \exp\left(\frac{-(y-y_0)^2}{\sigma_y^2}\right)\right)$$

where $f(A,u,v,x,y,\sigma_x,\sigma_y)$ is the filtering function, A is the amplitude of the function, i is the imaginary variable, x and y are the space variables and represent the spatial axes along which the image is collected, $x_0$ and $y_0$ are offsets in space that define the center of the Gaussian envelope and are typically set to the center of the Gabor wavelet window, u and v are the spatial frequencies of the complex exponential term and are typically set to some range of spatial frequencies that overlap with spatial frequencies that are likely to occur within the imaged tissue, and $\sigma_x$ and $\sigma_y$ are the standard deviations that define the width of the Gaussian envelope along the spatial axes. The real 1202 and imaginary parts are 2D sinusoids windowed by a 2D Gaussian function.

In some embodiments of the present inventive concept, x is typically mapped to the azimuth scan dimension and y is typically mapped to the depth dimension. If the range of x is −2 to 2 millimeters and the range of y is 0 to 2 mm, then $x_0$ is set to 0 mm and $y_0$ is set to 1 mm to center the Gabor wavelet in the image window. If spatially varying bands within the tissue have spatial frequencies ranging from 0.01 to 0.05 $mm^{-1}$ along the azimuthal dimension and 0.2 to 0.3 $mm^{-1}$ in the depth dimension, then an appropriate range for u would be 0.005 to 0.1 $mm^{-1}$ and an appropriate range for v would be 0.1 to 0.4 mm$^{-1}$. If the region that contains the bands is 1 mm in azimuth and 0.5 mm in depth, then $\sigma_x$ and $\sigma_y$ may be chosen such that that full width at half maximum of the Gaussian envelope covers this range.

Figure 13:
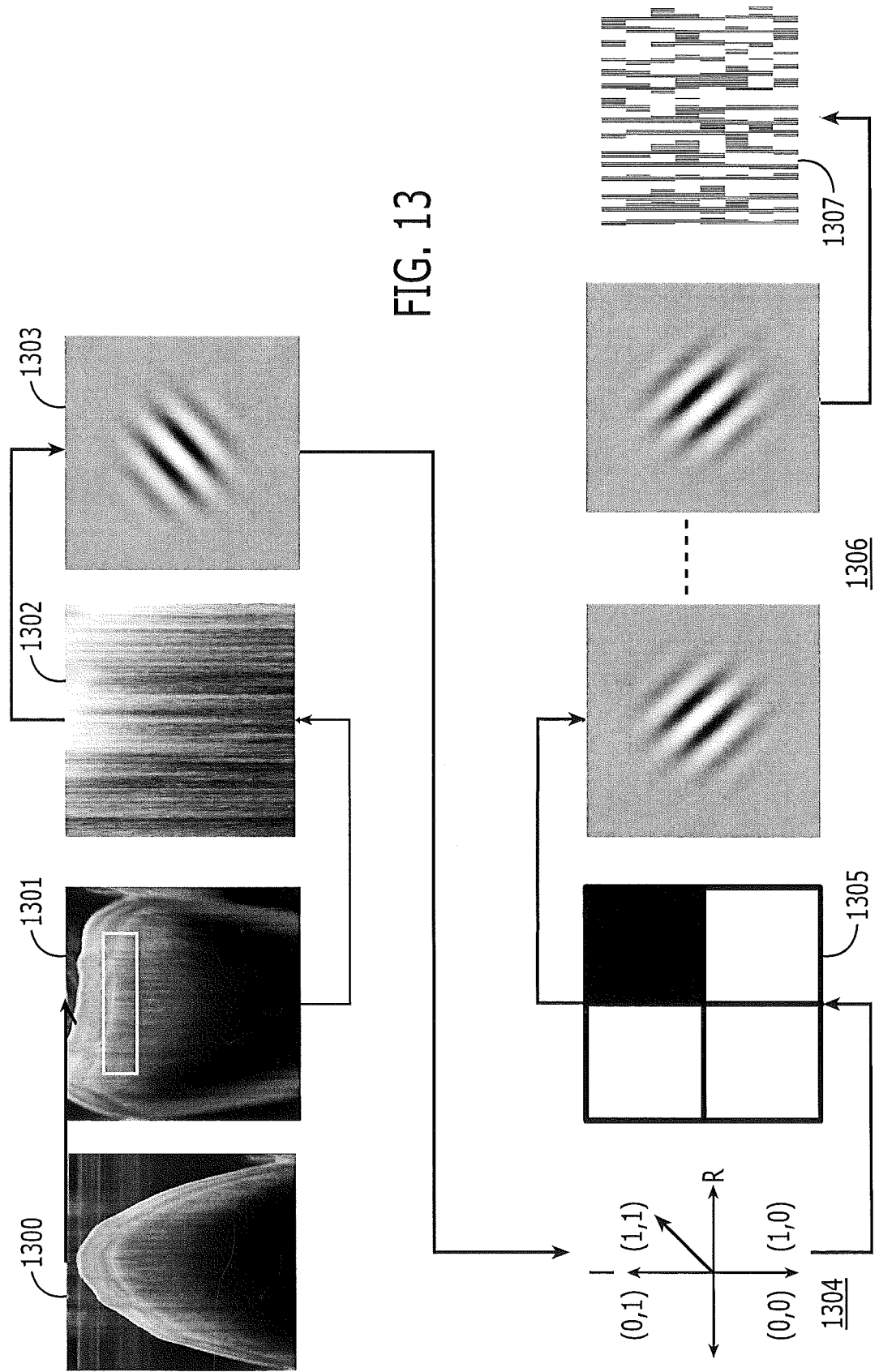
FIG. 13 is a diagram illustrating decision code generation according to some embodiments of the present inventive concept.

Referring now to FIG. 13, diagrams illustrating decision code generation according to some embodiments of the present inventive concept will be discussed. To generate a unique code based on the spatial frequency content of the fingernail bands 1300, the image is warped to flatten the nail 1301 and a region 1302 is extracted from that structure.

Scaled versions of a 2-D Gabor wavelet 1303 are applied to the extracted structure 1302. The Gabor wavelet may be cross-correlated with the flattened structure in the spatial dimension or the Fourier transforms of the Gabor wavelet and the flattened structure may be multiplied in the spatial frequency dimension.

The width of the light and dark bands within the extracted structure may be from about 0.13 mm to about 0.25 mm. Thus, the spatial frequency content of the Gabor filter should be varied in fine increments over multiple scales of the Nyquist limit, which in this case is may be about 0.065 mm$^{-1}$. The standard deviation of the Gaussian, $\sigma$, should be varied in multiple scales around the known width of the bands.

For each set of filter settings, a real and imaginary filtered image are generated by multiplying the 2D Gabor filter with the extracted bands. As discussed in Daugman, the phase quadrature response of the data to the filter set is extracted as:

$$h = h_{re} + i \cdot h_{im} \quad \text{[Eqn. 3]}$$

where $h_{re}$ is the sign of the integrated response to the real part of the Gabor filter and $h_{im}$ is the sign of the integrated response to the imaginary part. The phase of h yields coordinates in the complex plane that are mapped to bit pairs where (1,1), (0,1), (0,0), (1,0) are mapped to quadrants I-IV, respectively 1304.

The process is repeated across multiple scales of the spatial frequency filter 1306 to generate a binary code representative of image information content 1307.

Figure 14:
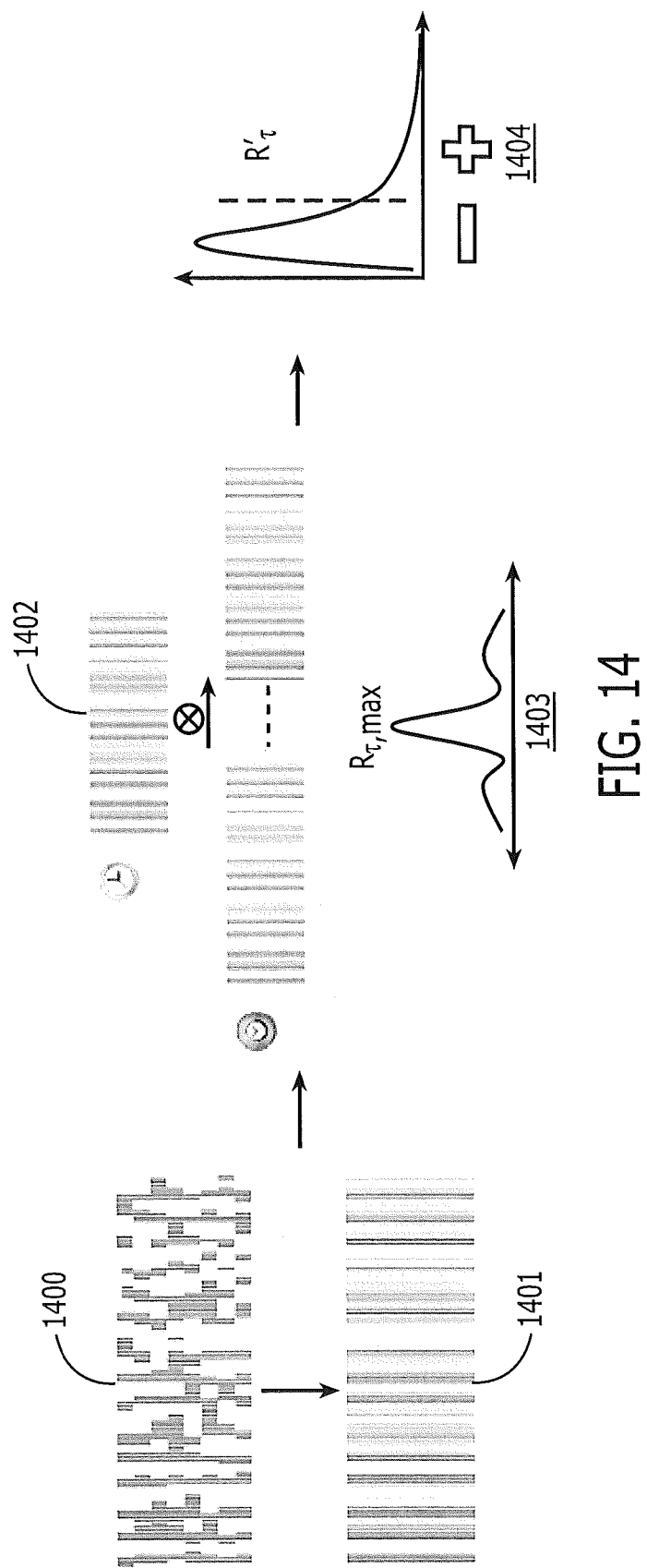
FIG. 14 is a diagram illustrating decision code processing and analysis according to some embodiments of the present inventive concept.

Referring now to FIG. 14, a diagram illustrating decision code processing and analysis according to some embodiments of the present inventive concept will be discussed. As illustrated therein, binary maps are reshaped from 2-dimensional arrays 1400 to 1-dimensional arrays 1401 and are compared using the Hamming distance as a measure of uniqueness 1402. The Hamming distance is:

$$d = \frac{A \oplus B}{\text{length}(A)} \quad \text{[Eqn. 4]}$$

where A and B are the binary maps and $\oplus$ is the exclusive or (XOR) operation. For each bit that is dissimilar, the XOR operation returns true, and as such the Hamming distance is greater for unique maps.

For two maps that are exactly the same, the Hamming distance should be about 0, a map processed with its inverse returns a Hamming distance of 1, and two randomly generated binary maps should return a Hamming distance of 0.5.

Similar comparison methods, such as the cross-correlation, can be applied to determine the relationship between codes 1403. The correlation peak may then be used to determine the similarity between codes.

A decision threshold can be generated based on a database of true positives and their resultant Hamming distance. For a given code generation method, the Hamming distance distribution 1404 will have a unique shape, and a decision line may be calculated to yield a desired sensitivity and specificity.

Figure 15:
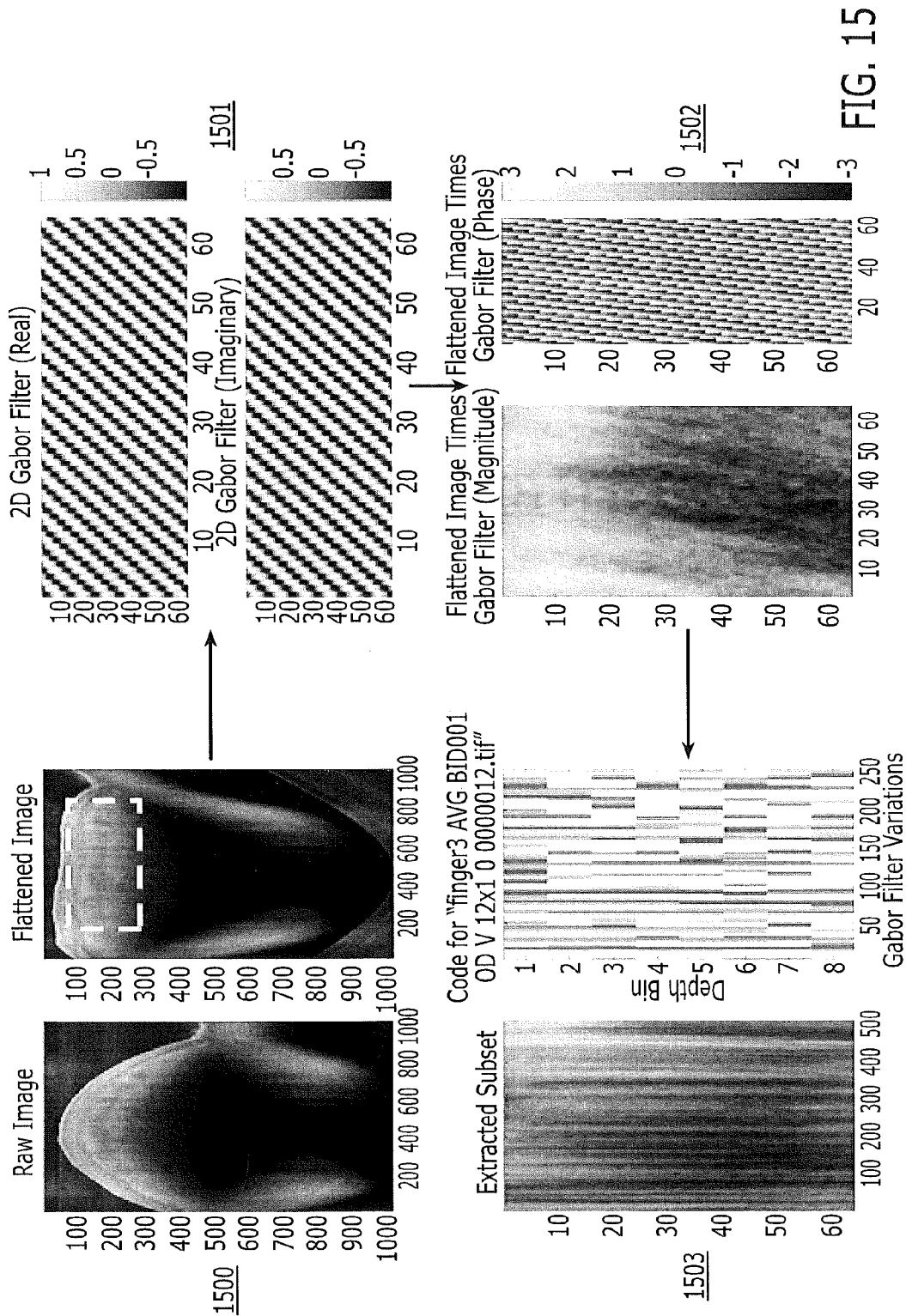
FIG. 15 is a diagram illustrating unique code generation from 1 slice plane through a 3D volume of fingernail bed data according to some embodiments of the present inventive concept.

Referring now to FIG. 15, a diagram illustrating unique code generation from a slice plane through a 3D volume of fingernail bed data according to some embodiments of the present inventive concept will be discussed. In particular, methods of slicing data to best analyze the spatial frequency content of the tissue topology under the fingernail bed will be discussed. Scans acquired orthogonal to the banded structure of the nail bed are flattened 1500 by finding the contour of the inner surface of the fingernail and warping the image based on the contour. A filter 1501 can then be applied to the data to extract or emphasize information content not readily available in the original image data. The banded structure can then be extracted from the area under the fingernail and processed 1502 to return a code 1503 unique to not only each individual but to each finger as well.

FIG. 15 illustrates the processing involved in the image analysis. The processing detailed above is applied to the extracted region, and a binary pair is generated for each set of filter values, yielding a map of bit values as illustrated in the code 1503 that is directly related to the unique spatial frequency content contained in each finger's pattern.

Figure 16:
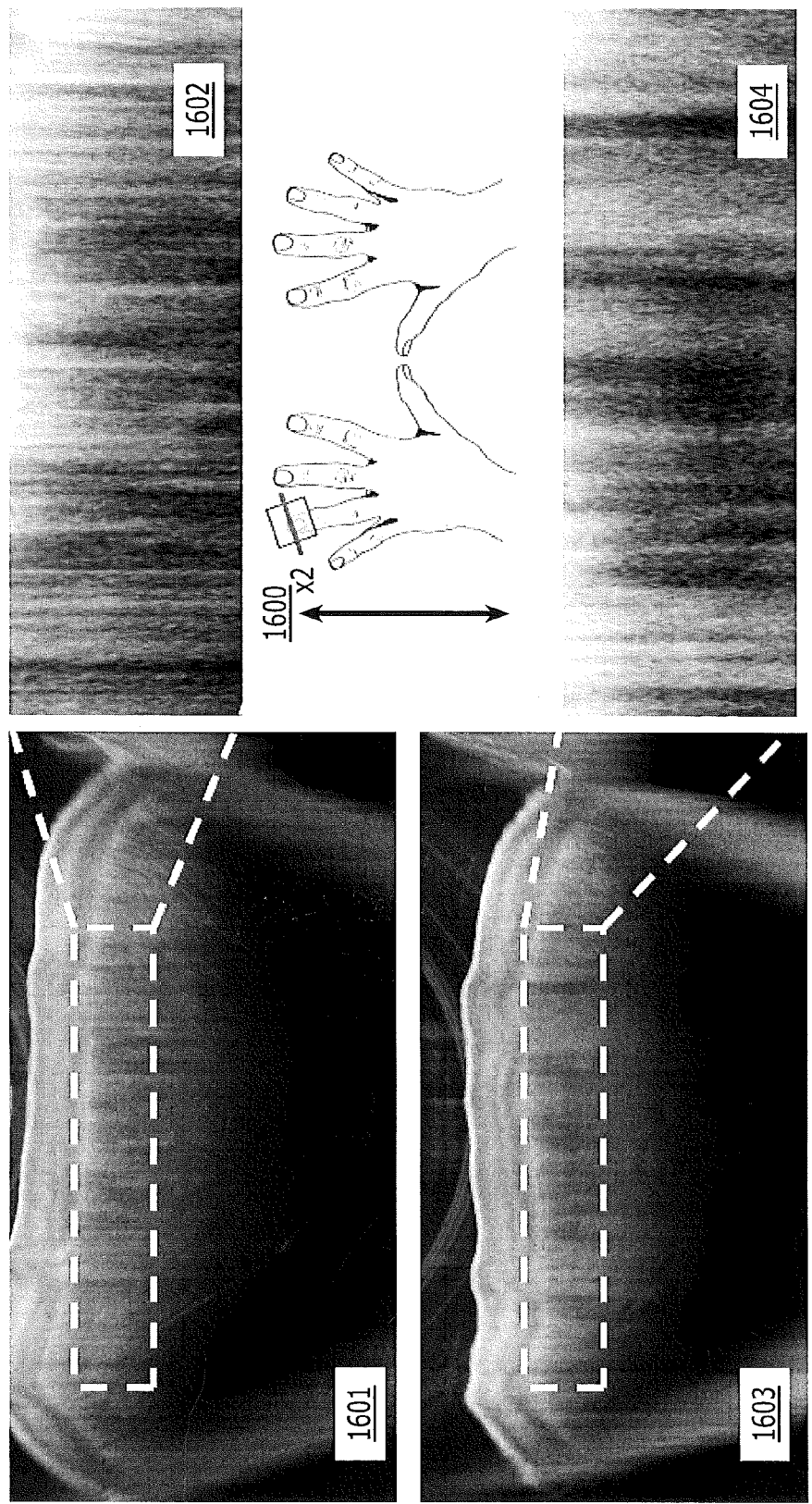
FIG. 16 is series of images illustrating OCT slices separated in time through finger 9 and the subsets used for unique, matching code generation according to some embodiments of the present inventive concept.

Referring now to FIG. 16, a series of images illustrating OCT slices separated in time through finger 9 and the subsets used for unique, matching code generation according to some embodiments of the present inventive concept will be discussed. A depth slice may be acquired from one finger 1600 at two different time points 1601, 1603 and subsets 1602, 1604 from the two slices can be analyzed to determine the Hamming distance for identical finger scans as a function of time. After acquisition of many such scans, the Hamming distance range for unique fingers may be statistically determined for large data sets.

Figure 17:
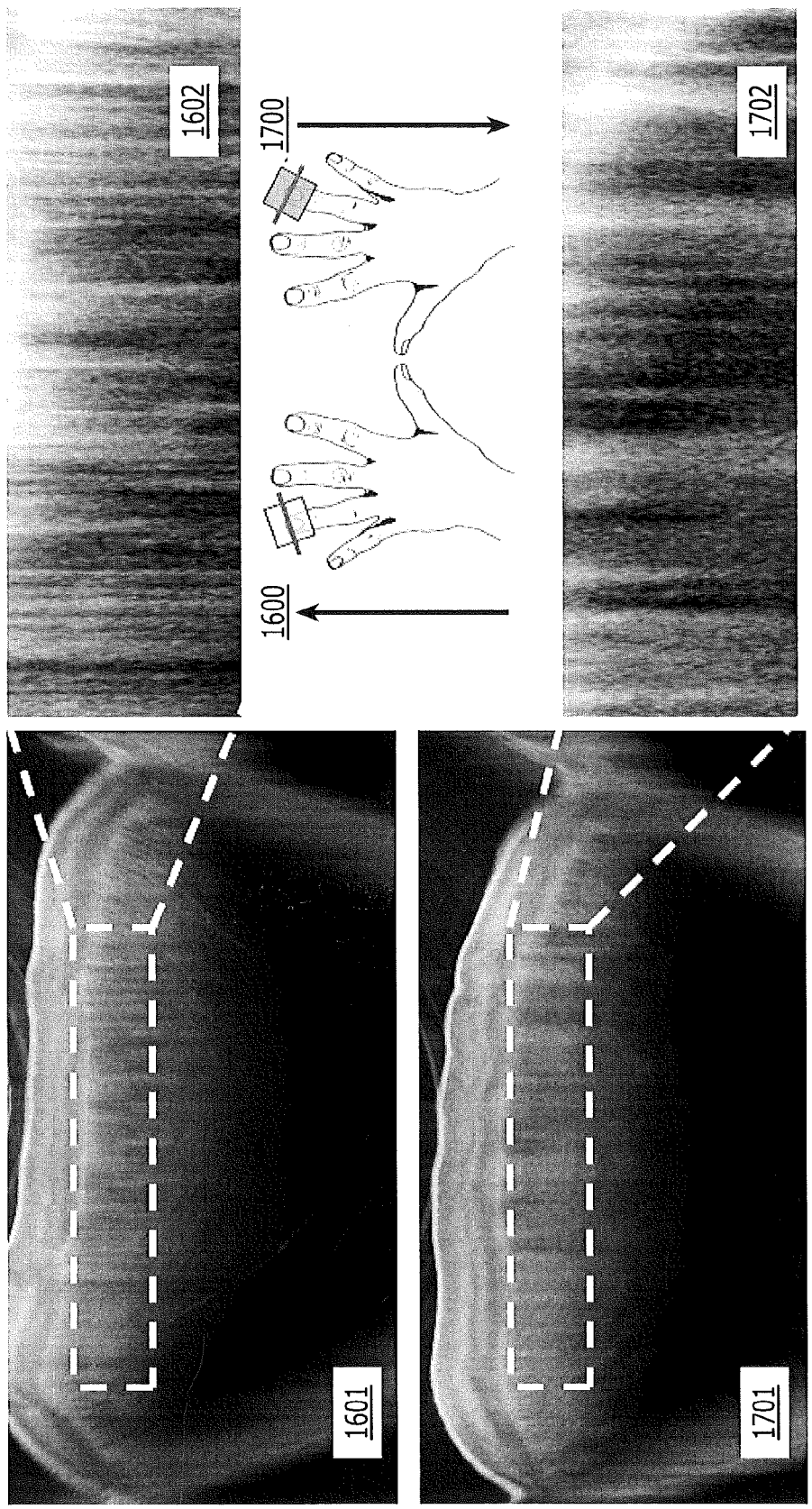
FIG. 17 is a series of images illustrating OCT slices from fingers 9 and 4 and the subsets used for unique, non-matching code generation according to some embodiments of the present inventive concept.

Referring now to FIG. 17, a series of images illustrating OCT slices from fingers 9 and 4 and the subsets used for unique, non-matching code generation according to some embodiments of the present inventive concept will be discussed. Depth slices 1601, 1701 may be acquired from two unique fingers 1600, 1700 on different hands and subsets 1602, 1702 from the two slices can be analyzed to determine the Hamming distance for different fingers. After acquisition of many such scans, the Hamming distance range for uniquely different fingers on different hands may be statistically determined for large data sets.

Figure 18:
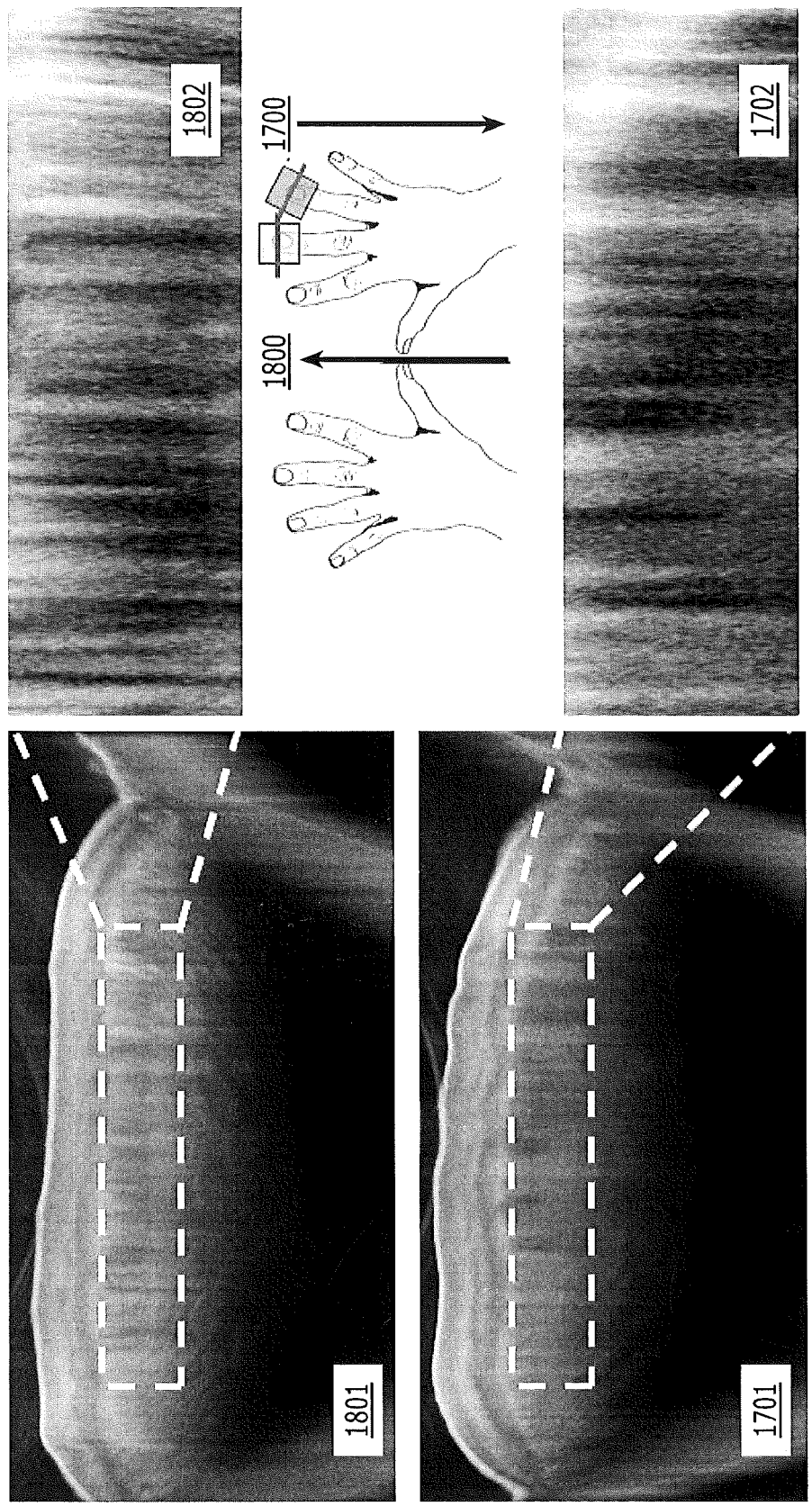
FIG. 18 is a series of images illustrating OCT slices from fingers 3 and 4 and the subsets used for unique, non-matching code generation according to some embodiments of the present inventive concept.

Referring now to FIG. 18, a series, of images illustrating OCT slices from fingers 3 and 4 and the subsets used for unique, non-matching code generation according to some embodiments of the present inventive concept will be discussed. Depth slices 1701, 1801 may be acquired from two unique fingers 1700, 1800 on the same hand and subsets 1702, 1802 from the two slices can be analyzed to determine the Hamming distance for different fingers on the same hand. After acquisition of many such scans, the Hamming distance range for uniquely different fingers on the same hand may be statistically determined for large data sets.

A database may be generated from many codes captured from the same finger as a function of time to determine the variability in the Hamming distance as a function of time and unique spatial position scanned to determine the range of Hamming distances that may be assigned to a positive identification.

A database may be generated from many codes captured from different fingers as a function of time to determine the variability in the Hamming distance as a function of time and unique spatial content to determine the range of Hamming distances likely in a negative identification.

The true positive and true negative ranges may be modeled by a normal distribution to approximate the false positive and false negative ranges.

A receiver operating characteristic (ROC) curve may be generated based on the true positives and estimated false positives to highlight the sensitivity and specificity of the code as implemented.

Figure 19:
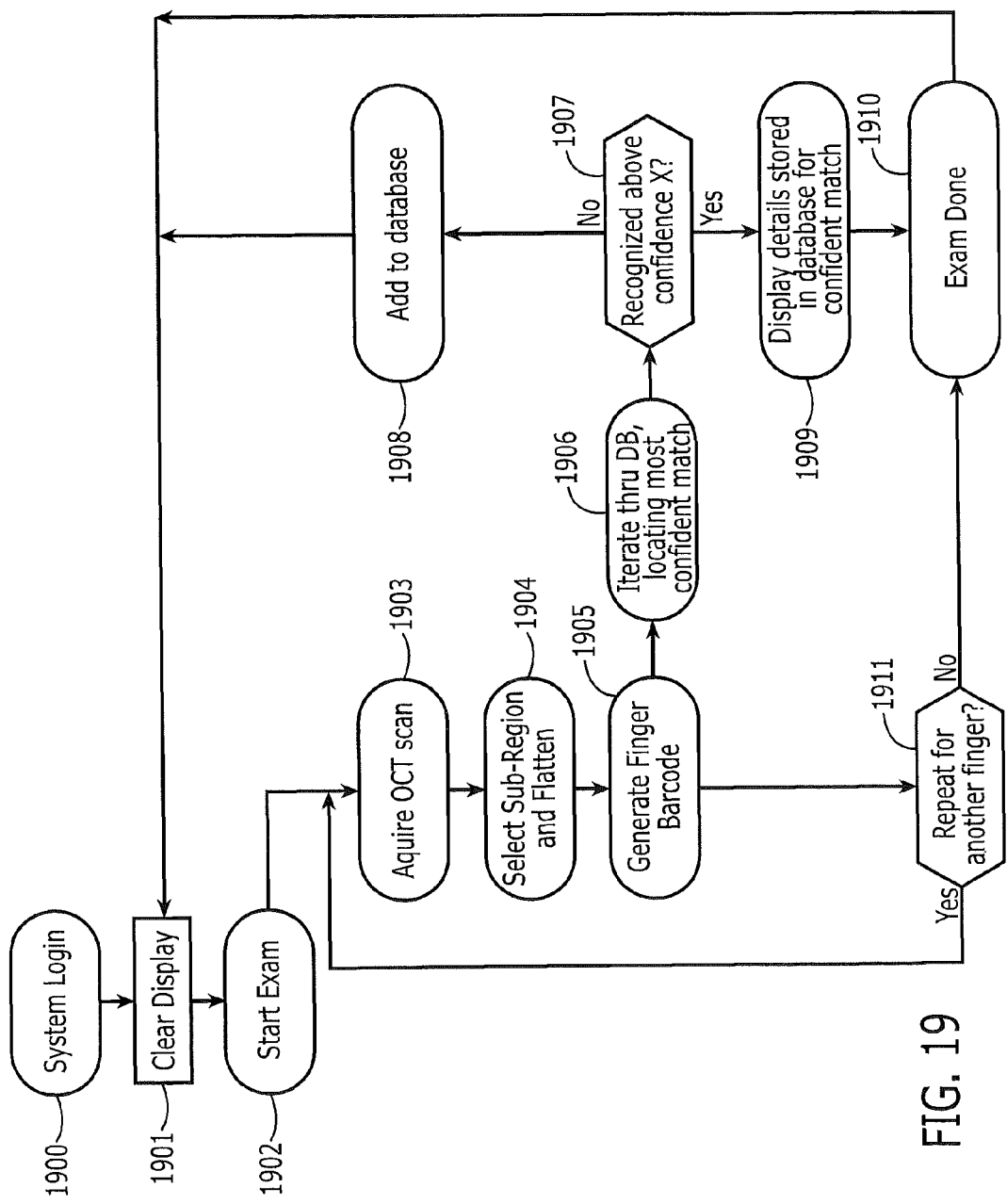
FIG. 19 is a flowchart illustrating processing steps in high-throughput biometric identification in accordance with some embodiments of the present inventive concept.

Referring now to FIG. 19, a flowchart illustrating processing steps in high-throughput biometric identification in accordance with some embodiments of the present inventive concept will be discussed. Operates begin at block 1900 by logging into the system. After logging into the security system (block 1900), the display will be cleared (block 1901) and the user will be prompted to start the exam (block 1902). The subject will place one or more fingers in the path of the scan beam and the necessary OCT data will be acquired (block 1903). This data will then be processed by extracting a subregion of the OCT image (block 1904) and generating the code (block 1905) associated with each unique finger. Smart search algorithms will examine a database of stored binary maps to determine if a match exists within the database (block 1906). If a match exists (block 1906) and the match is recognized above a threshold confidence level (block 1907), the software will display relevant subject information to the user (block 1909). If no match exists within the database (block 1907), the option will be presented to the user to add the subject to the database (block 1908). It will be determined if another finger needs to be examined (block 1911). If another finger needs to be examined (block 1911), operations return to block 1903 and repeat. If, on the other hand, no other fingers need to be examined, operations of the exam may terminate (block 1910). In some embodiments, the software may be expanded to incorporate advanced security measures, which would include but not be limited to interfacing to national security software for more detailed subject information such as any outstanding warrants or alerting law enforcement if a wanted subject has been identified. The results, consisting of either the processed OCT data and the resultant code or only the resultant code may be stored on a local or networked computer.

Figure 20:
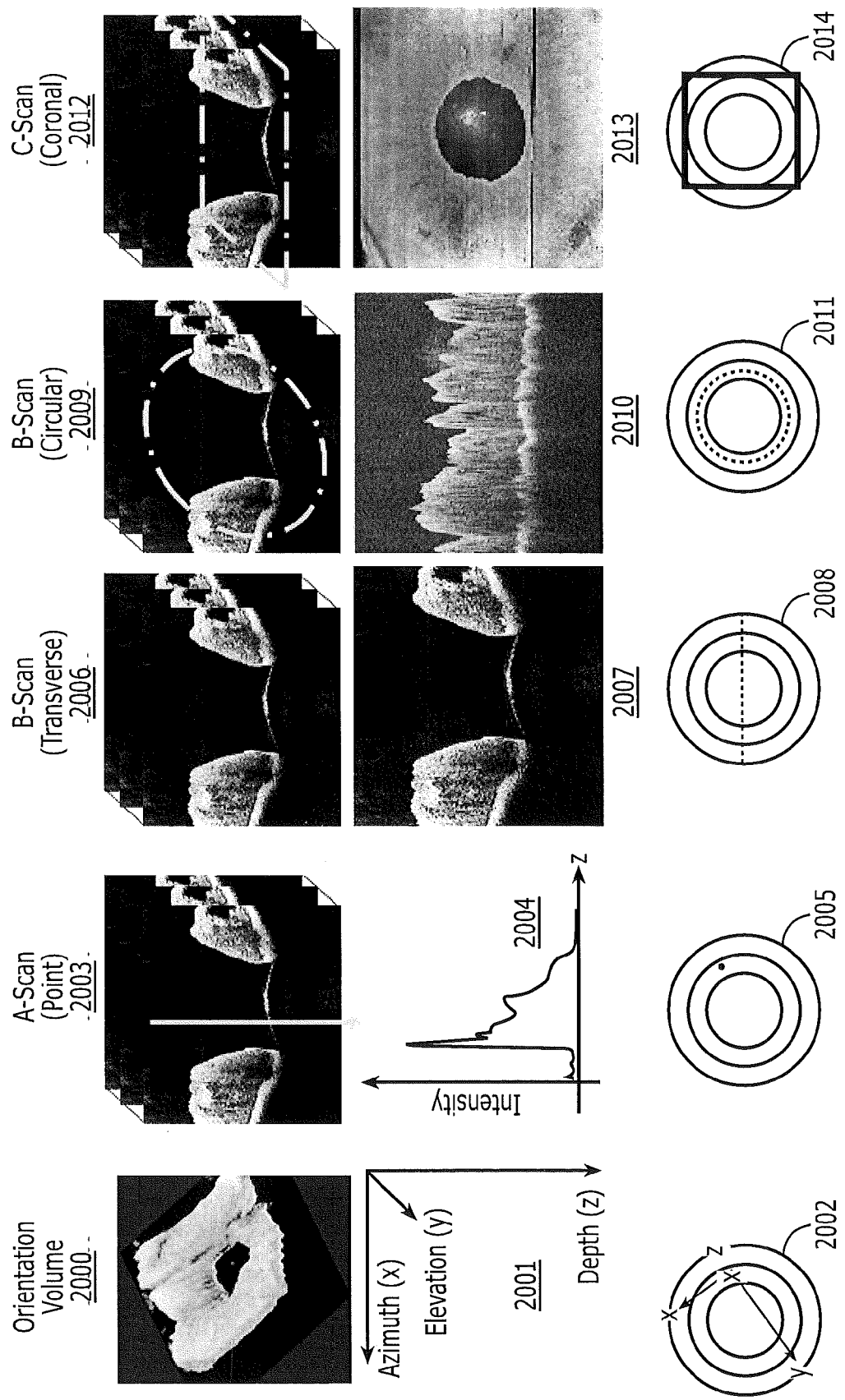
FIG. 20 a diagram illustrating a series of slice planes through a 3D volume in the iris and representative OCT images from said planes according to some embodiments of the inventive concept.

Referring to FIG. 20, a series of slice planes through a 3D volume in the iris and representative OCT images from said planes according to some embodiments of the inventive concept will be discussed. Some embodiments involve the generation of a unique code from a 2-dimensional slice 2006 through a 3-dimensional volume 2000 acquired at the iris. The orientation axes 2001 and corresponding iris orientation 2002 are detailed in FIG. 20. A single depth line 2003 (A-Scan) provides an intensity profile 2004 at a single, spatially unique scan position 2005. Transverse B-Scan slices 2006 provide images as a function of azimuth and depth 2007 through the iris 2008. Circular slices through the structure 2009 provide B-Scan images 2010 through the iris 2011. Once an FDOCT volume has been acquired, coronal slices 2012 and corresponding C-Scan images 2013 can be reconstructed for the iris 2014. In some embodiments of the present inventive concept, a raster scan orthogonal to the banded structure in the fingernail bed may be used. By acquiring multiple scans orthogonal to the bands in the bed at different positions across the nail, a volume of data 2000 is generated. Generating a projection along the depth axis returns a volume intensity projection. Some embodiments of the present inventive concept improve upon conventional methods by the addition of the depth dimension, which permits multiple methods of analysis.

Figure 21:
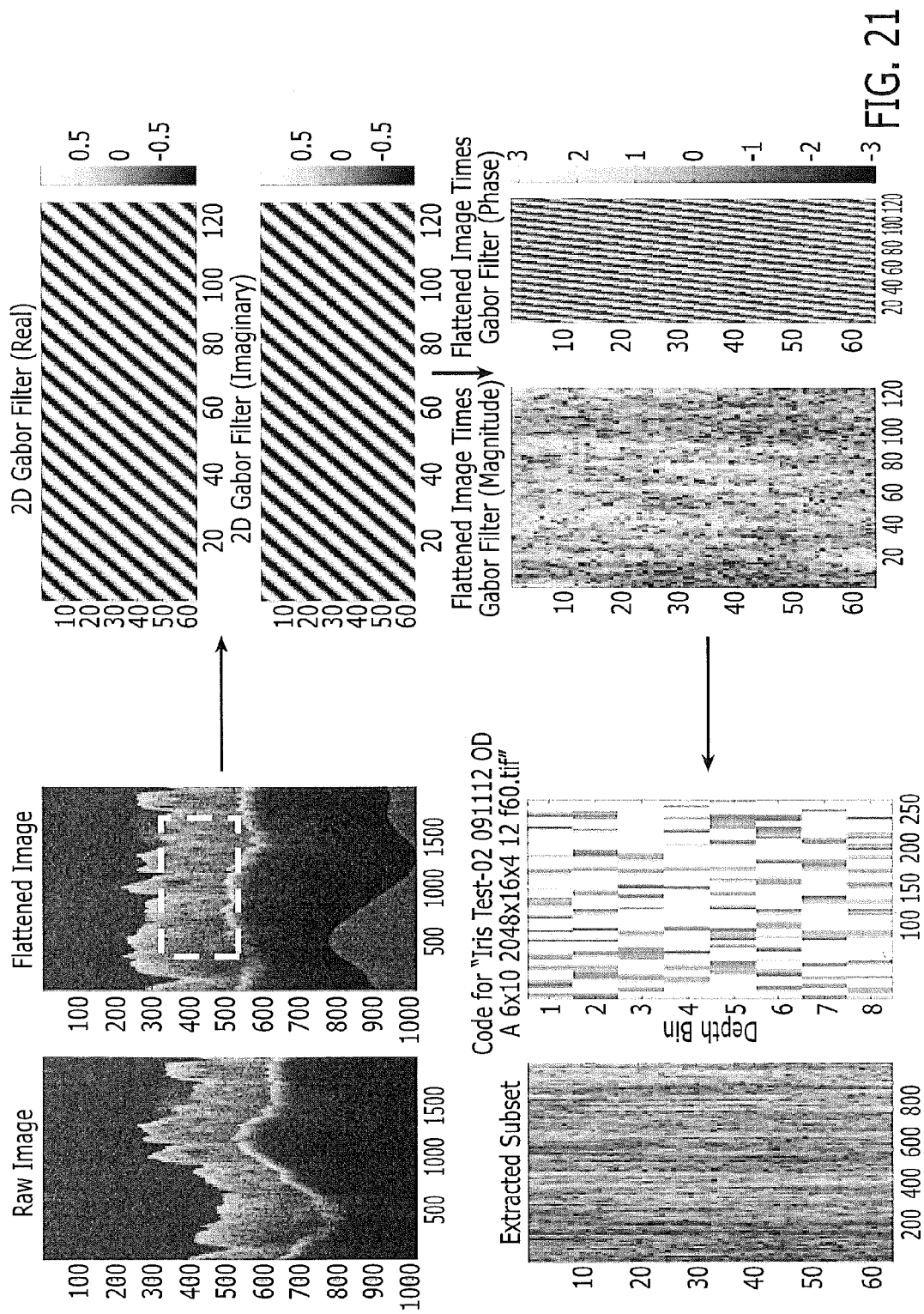
FIG. 21 are diagrams of unique code generation from 1 slice through a 3D volume of iris data according to some embodiments of the inventive concept.

Referring now to FIG. 21, diagrams of unique code generation from 1 slice through a 3D volume of iris data according to some embodiments of the inventive concept will be discussed. In particular, methods of slicing data to best analyze the spatial frequency content of the tissue topology of the iris will be discussed. Circular scans acquired at the iris are flattened 2100 by finding the contour of the inner surface of the iris and warping the image based on the contour. A filter 2101 can then be applied to the data to extract or emphasize information content not readily available in the original image data. The fine structure can then be extracted from the iris and processed 2102 to return a code 2103 unique to not only each individual but to each eye as well.

The code generated by some embodiments of the present inventive concept may be used to aid in subject identification. This code could be included with any form of personal identification, such as a passport or government-issued ID, as an additional security measure. As such, the code could be, for example, read by a barcode scanner interfaced to the OCT database to aid in rapid identification and screening in high-traffic security checkpoints.

While some embodiments of the present inventive concept are discussed above, other embodiments may also be envisioned without departing from the scope of the present inventive concept. For example, further embodiments of the present inventive concept are illustrated in FIGS. 1106, 1109, and 1112. In particular, a slice orthogonal to the depth axis 1112 would return the band pattern as seen from the nail. A slice 1106, would yield a side-long view of the banded structure. Sampling more densely in this dimension could allow for better resolution of the spatial frequency content contained in the bands. With the volume of data, it may be possible to analyze the data using embodiments discussed herein and then use an additional implementation, such as the analysis using slices 1106, to improve the confidence level of the result.

Furthermore, traditional fingerprint data may be collected using systems according to some embodiments of the present inventive concept. An SDOCT volume may be acquired over the finger tip; the volume projection of such a volume would yield an image containing traditional fingerprint data. In further embodiments, this data could be acquired by scanning the top of the nail with the SDOCT system while at the same time capturing an image of the finger tip using a standard still or video camera. With both data types captured concurrently, the new SDOCT-generated biometric could be correlated with and stored alongside traditional fingerprint data contained in law enforcement databases, facilitating easier integration into current security systems.

As discussed briefly above, methods, systems and computer program products for biometric identification by human fingernail bed imaging using SDOCT are non-invasive methods, systems and computer program products for acquiring a novel biometric identifier that is relatively insensitive to obfuscation by cosmetic means. This technology is synergistic with traditional fingerprint identification systems and could interface with said systems easier than other biometric technologies.

As discussed above, data acquired using systems and methods according to some embodiments of the present inventive concept may be processed using a computer system 140 (data processing system). Exemplary embodiments of a data processing system 2230 configured in accordance with embodiments of the present inventive concept will be discussed with respect to FIG. 22. The data processing system 2230 may include a user interface 2244, including, for example, input device(s) such as a keyboard or keypad, a display, a speaker and/or microphone, and a memory 2236 that communicate with a processor 2238. The data processing system 2230 may further include I/O data port(s) 2246 that also communicates with the processor 2238. The I/O data ports 2246 can be used to transfer information between the data processing system 2230 and another computer system or a network using, for example, an Internet Protocol (IP) connection. These components may be conventional components such as those used in many conventional data processing systems, which may be configured to operate as described herein.

Figure 22:
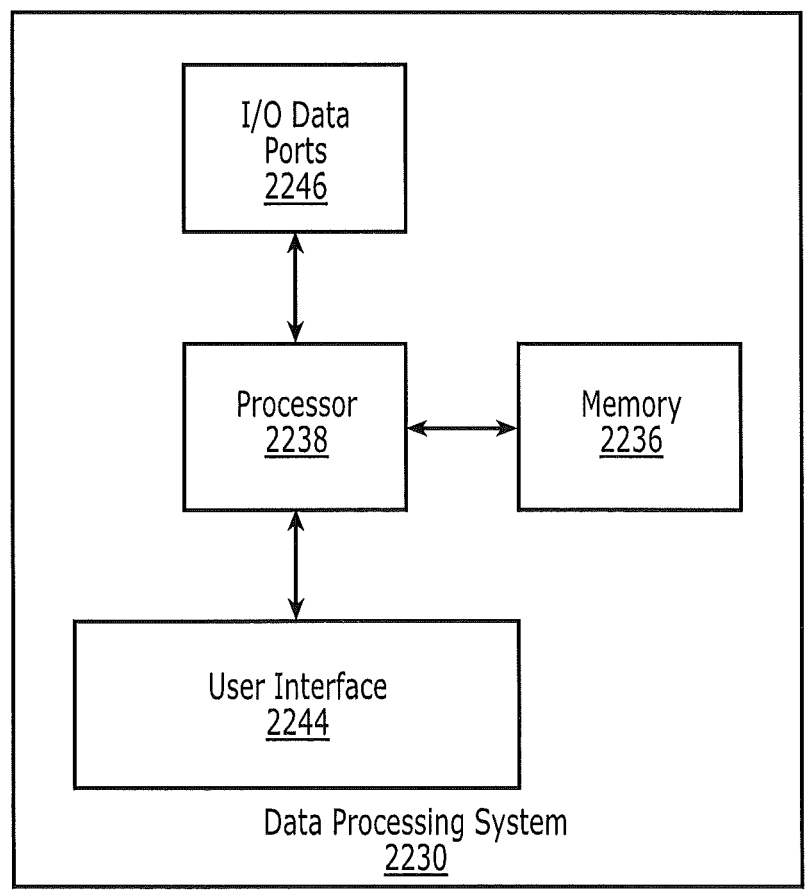
FIG. 22 is a block diagram of a data processing system suitable for use in some embodiments of the present inventive concept.
Figure 23:
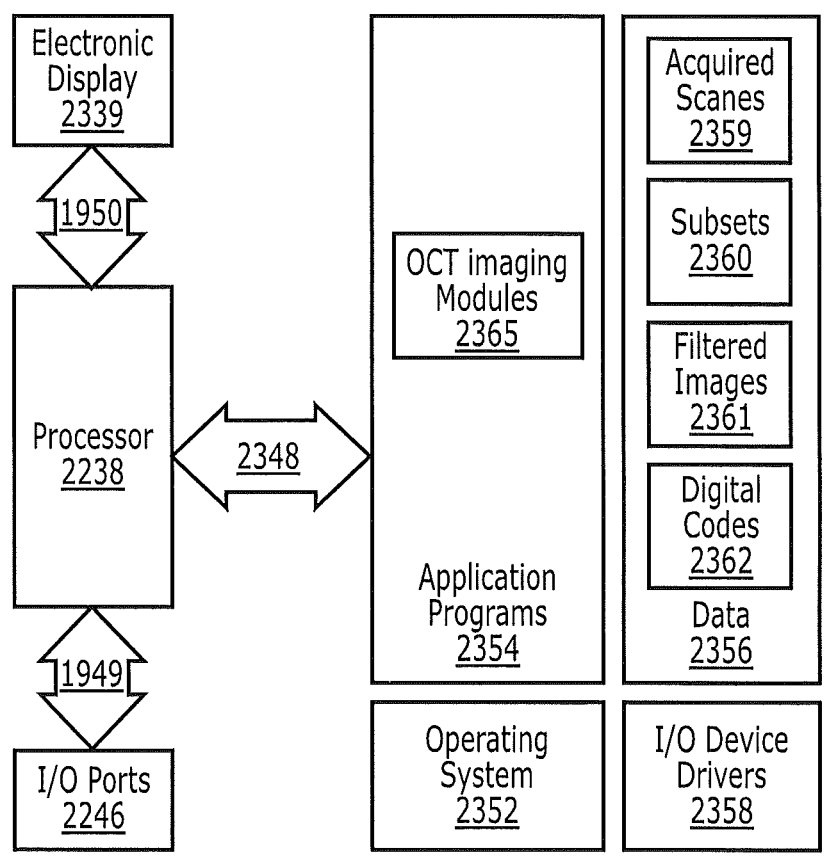
FIG. 23 is a more detailed block diagram of a system according to some embodiments of the present inventive concept.

Referring now to FIG. 23, a more detailed block diagram of a data processing system of FIG. 22 is provided that illustrates systems, methods, and computer program products in accordance with some embodiments of the present inventive concept, which will now be discussed. As illustrated in FIG. 23, the processor 2238 communicates with the memory 2236 via an address/data bus 2348, the I/O data ports 2246 via address/data bus 2349 and the electronic display 2339 via address/data bus 2350. The processor 2238 can be any commercially available or custom enterprise, application, personal, pervasive and/or embedded microprocessor, microcontroller, digital signal processor or the like. The memory 2236 may include any memory device containing the software and data used to implement the functionality of the data processing system 2230. The memory 2236 can include, but is not limited to, the following types of devices: ROM, PROM, EPROM, EEPROM, flash memory, SRAM, and DRAM.

As further illustrated in FIG. 23, the memory 2236 may include several categories of software and data used in the system: an operating system 2352; application programs 2354; input/output (I/O) device drivers 2358; and data 2356. As will be appreciated by those of skill in the art, the operating system 2352 may be any operating system suitable for use with a data processing system, such as OS/2, AIX or zOS from International Business Machines Corporation, Armonk, N.Y., Windows95, Windows98, Windows2000 or WindowsXP, or Windows CE or Windows 7 from Microsoft Corporation, Redmond, Wash., Palm OS, Symbian OS, Cisco IOS, VxWorks, Unix or Linux. The I/O device drivers 2358 typically include software routines assessed through the operating system 2352 by the application programs 2354 to communicate with devices such as the I/O data port(s) 2246 and certain memory 2236 components. The application programs 2354 are illustrative of the programs that implement the various features of the some embodiments of the present inventive concept and may include at least one application that supports operations according to embodiments of the present inventive concept. Finally, as illustrated, the data 2356 may include acquired scans 2359, subsets 2360, filtered images 2361 and codes 2362, which may represent the static and dynamic data used by the application programs 2354, the operating system 2352, the I/O device drivers 2358, and other software programs that may reside in the memory 2236.

As further illustrated in FIG. 23, according to some embodiments of the present inventive concept, the application programs 2354 include OCT imaging modules 2365. While the present inventive concept is illustrated with reference to OCT imaging modules 2365 as being application programs in FIG. 23, as will be appreciated by those of skill in the art, other configurations fall within the scope of the present inventive concept. For example, rather than being application programs 2354, these circuits and modules may also be incorporated into the operating system 2352 or other such logical division of the data processing system. Furthermore, while the OCT imaging modules 2365 are illustrated in a single system, as will be appreciated by those of skill in the art, such functionality may be distributed across one or more systems. Thus, the present inventive concept should not be construed as limited to the configuration illustrated in FIG. 23, but may be provided by other arrangements and/or divisions of functions between data processing systems. For example, although FIG. 23 is illustrated as having various circuits, one or more of these circuits may be combined without departing from the scope of the present inventive concept.

It will be understood that the OCT imaging modules 2365 may be used to implement various portions of the present inventive concept capable of being performed by a data processing system. For example, the OCT imaging modules may be used to process and assess the images produced by the OCT system according to some embodiments of the present inventive concept.

Example embodiments are described above with reference to block diagrams and/or flowchart illustrations of methods, devices, systems and/or computer program products. It is understood that a block of the block diagrams and/or flowchart illustrations, and combinations of blocks in the block diagrams and/or flowchart illustrations, can be implemented by computer program instructions. These computer program instructions may be provided to a processor of a general purpose computer, special purpose computer, and/or other programmable data processing apparatus to produce a machine, such that the instructions, which execute via the processor of the computer and/or other programmable data processing apparatus, create means (functionality) and/or structure for implementing the functions/acts specified in the block diagrams and/or flowchart block or blocks.

These computer program instructions may also be stored in a computer-readable memory that can direct a computer or other programmable data processing apparatus to function in a particular manner, such that the instructions stored in the computer-readable memory produce an article of manufacture including instructions which implement the functions/acts specified in the block diagrams and/or flowchart block or blocks.

The computer program instructions may also be loaded onto a computer or other programmable data processing apparatus to cause a series of operational steps to be performed on the computer or other programmable apparatus to produce a computer-implemented process such that the instructions which execute on the computer or other programmable apparatus provide steps for implementing the functions/acts specified in the block diagrams and/or flowchart block or blocks.

Accordingly, example embodiments may be implemented in hardware and/or in software (including firmware, resident software, micro-code, etc.). Furthermore, example embodiments may take the form of a computer program product on a computer-usable or computer-readable storage medium having computer-usable or computer-readable program code embodied in the medium for use by or in connection with an instruction execution system. In the context of this document, a computer-usable or computer-readable medium may be any medium that can contain, store, communicate, propagate, or transport the program for use by or in connection with the instruction execution system, apparatus, or device.

The computer-usable or computer-readable medium may be, for example but not limited to, an electronic, magnetic, optical, electromagnetic, infrared, or semiconductor system, apparatus, device, or propagation medium. More specific examples (a non-exhaustive list) of the computer-readable medium would include the following: an electrical connection having one or more wires, a portable computer diskette, a random access memory (RAM), a read-only memory (ROM), an erasable programmable read-only memory (EPROM or Flash memory), an optical fiber, and a portable compact disc read-only memory (CD-ROM). Note that the computer-usable or computer-readable medium could even be paper or another suitable medium upon which the program is printed, as the program can be electronically captured, via, for instance, optical scanning of the paper or other medium, then compiled, interpreted, or otherwise processed in a suitable manner, if necessary, and then stored in a computer memory.

Computer program code for carrying out operations of data processing systems discussed herein may be written in a high-level programming language, such as Java, AJAX (Asynchronous JavaScript), C, and/or C++, for development convenience. In addition, computer program code for carrying out operations of example embodiments may also be written in other programming languages, such as, but not limited to, interpreted languages. Some modules or routines may be written in assembly language or even micro-code to enhance performance and/or memory usage. However, embodiments are not limited to a particular programming language. It will be further appreciated that the functionality of any or all of the program modules may also be implemented using discrete hardware components, one or more application specific integrated circuits (ASICs), or a field programmable gate array (FPGA), or a programmed digital signal processor, a programmed logic controller (PLC), or microcontroller.

It should also be noted that in some alternate implementations, the functions/acts noted in the blocks may occur out of the order noted in the flowcharts. For example, two blocks shown in succession may in fact be executed substantially concurrently or the blocks may sometimes be executed in the reverse order, depending upon the functionality/acts involved. Moreover, the functionality of a given block of the flowcharts and/or block diagrams may be separated into multiple blocks and/or the functionality of two or more blocks of the flowcharts and/or block diagrams may be at least partially integrated.

In some embodiments of the present inventive concept, the unique reference code generated for a sample may be used in making a diagnostic decision. In particular, the reference codes may be indicative of a class of objects. As used herein, a "class of objects" refers to any object for which a multiple dimensional image can be acquired and a unique code can be generated. The class of objects may be defined by a regular structure that is nominally time invariant. As discussed above, "time invariant" refers to a property that does not change over a time period of interest. For example, the class of objects may include a physical state, a physical object (an integrated circuit, a printed circuit board, etc.), human tissue and the like. Each class of objects has a reference code, which is derived from aggregate data.

The subject of the image is not time-invariant. Thus, a unique reference code may be generated for the subject being imaged and this reference code can be compared to reference codes for each class. The result of this comparison can be used to provide a diagnosis. For example, if the subject being imaged is a circuit board, embodiments discussed herein may be used for pattern recognition. Thus, if a trace on the circuit board is broken or out of place, this diagnosis can be made. For a human subject, it may be determined that a subject falls into a certain class or the subject's class has changed over time. Falling into the class or a change of class may be indicative of a disease state or of disease progression.

Thus, a state is a condition of being that is identifiable and has attributes that can be captured in a multidimensional image. The state must be sufficiently consistent over time to have meaning. Accordingly, embodiments of the inventive concept may be used to diagnose diseases in a human subject, identify manufacturing failures in a manufactured product, identify people using facial recognition and the like as will be discussed further below with respect to FIGS. 24 through 37.

Figure 24:
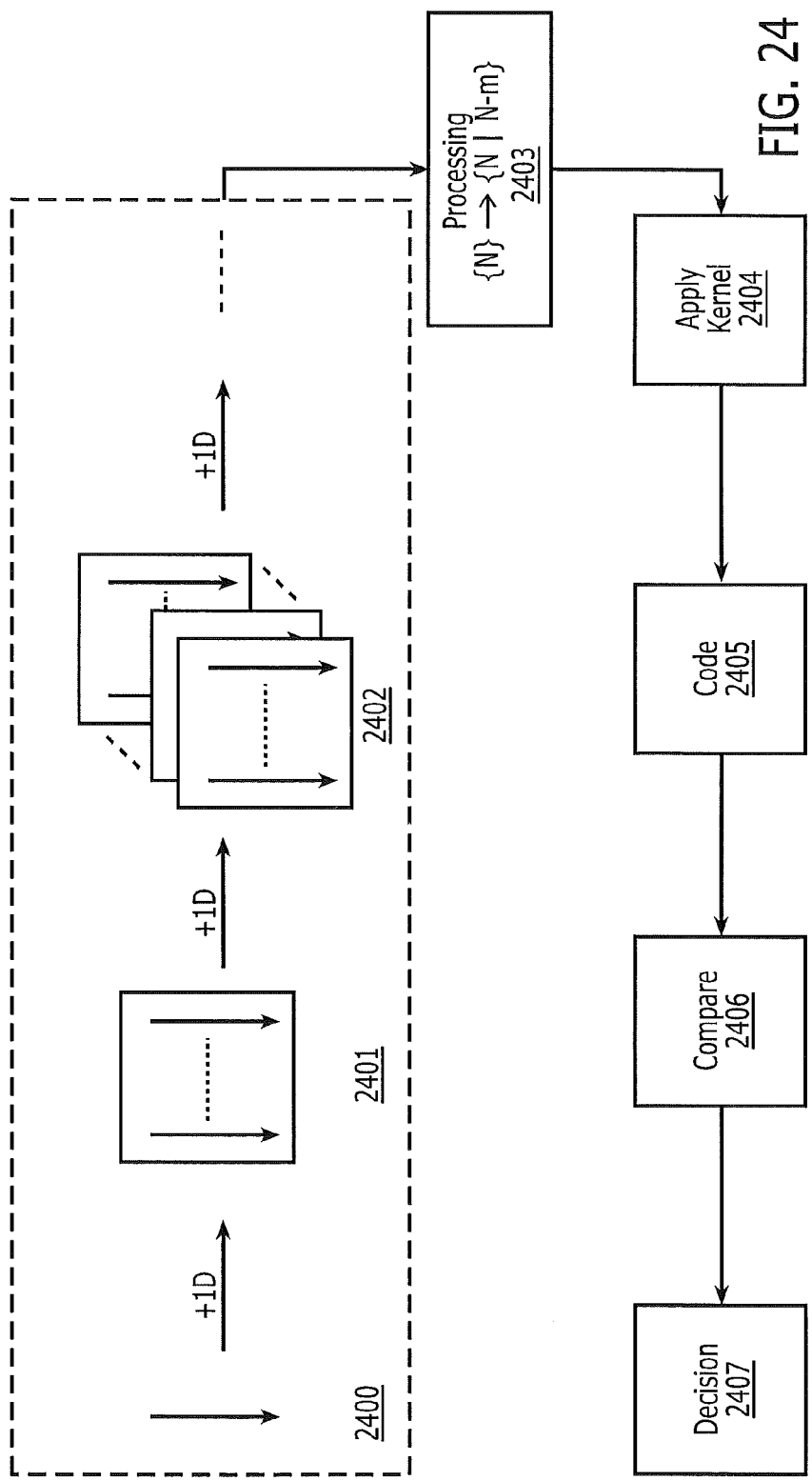
FIG. 24 is a block diagram illustrating processing of N-dimensional data in accordance with some embodiments of the present inventive concept.

Referring first to FIG. 24, a block diagram illustrating processing N-Dimensional data in accordance with some embodiments of the present inventive concept will be discussed. As illustrated in FIG. 24, N-Dimensional data 2400, 2401, 2402 can be processed as-is or collapsed to a lower dimensional order 2403 with a kernel operation 2404 that extracts unique identifiers from the data set 2403 and generates a unique code 2405 associated with the data set 2403. This code can then be compared 2406 with other unique identifier codes and a decision 2407 can be made based on the relationship between the code generated 2405 and the reference code or codes.

Figure 25:
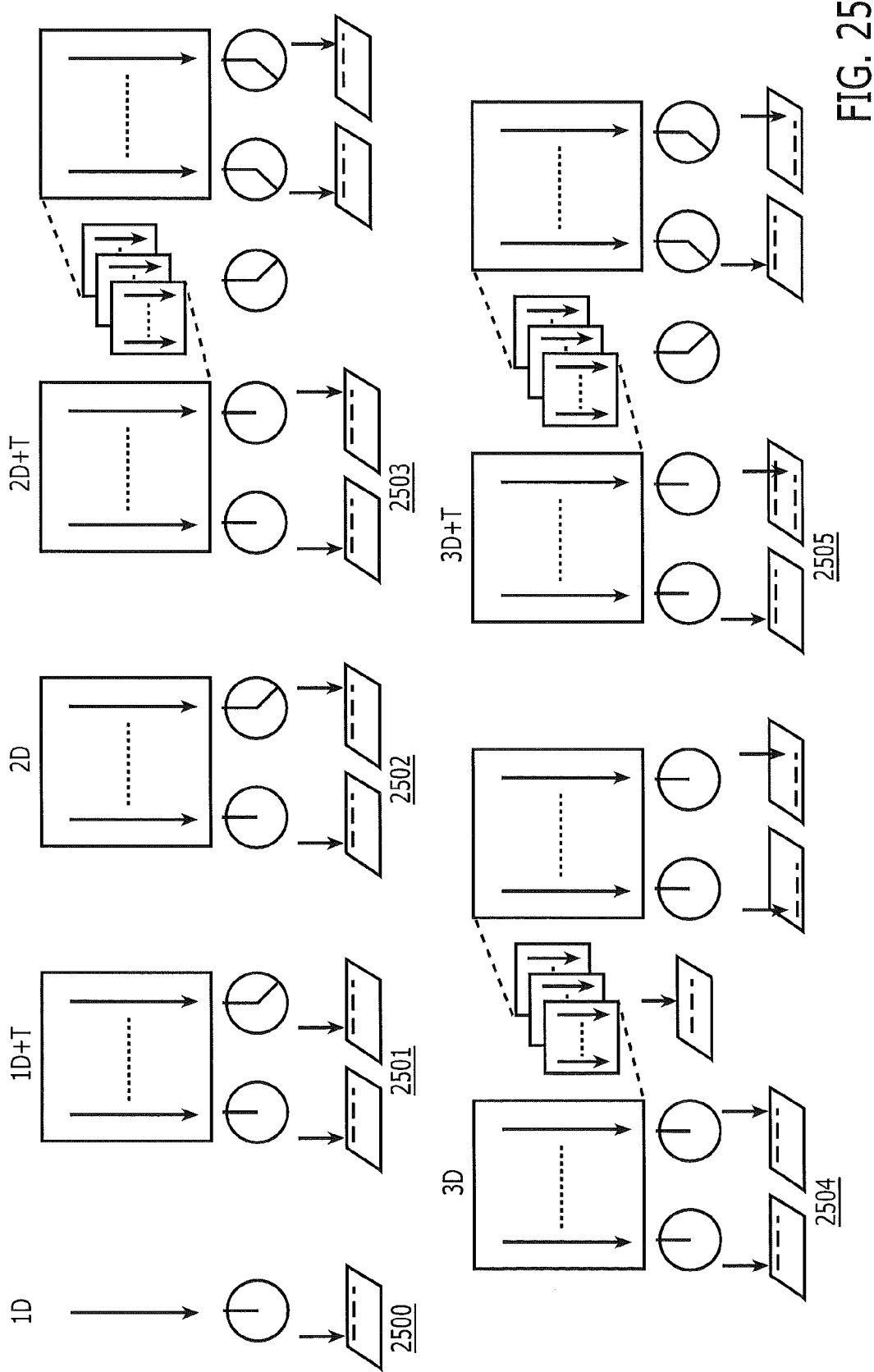
FIG. 25 is a block diagram illustrating processing of N-dimensional data in accordance with some embodiments of the present inventive concept.

Referring now to FIG. 25, data to be processed 2403 (FIG. 24) can be N-Dimensional. For example, the data to be processed 2403 may be 1 dimensional 2500, i.e., originating from one unique location in space; 1 dimensional+Time 2501, i.e., originating from one unique location in space as measured over some finite period of time; 2 dimensional 2502, i.e., originating from multiple spatial locations along a plane or surface; 2 dimensional+Time 2503, i.e., originating from a plane or surface as measured over some finite period of time; 3 dimensional 2504, i.e., originating from multiple spatial locations contained within a three dimensional volume; or 3 dimensional+Time 2505, i.e., originating from multiple spatial locations contained within a three dimensional volume as measured over some finite period of time. It will be understood that this dimensional data is provide for example only and that embodiments of the present inventive concept are not limited thereto.

Figure 26:
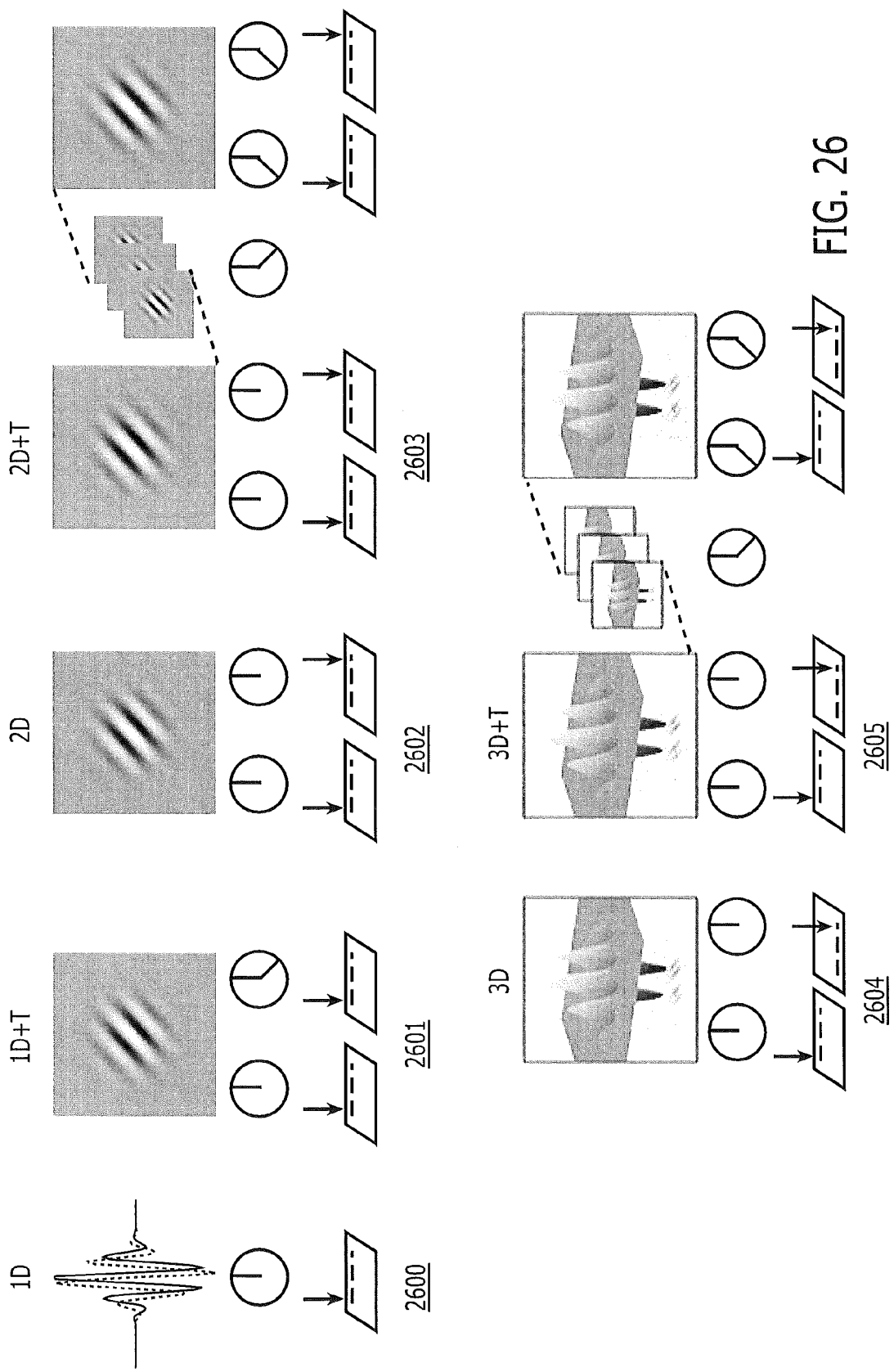
FIG. 26 is a block diagram illustrating processing of N-dimensional data in accordance with some embodiments of the present inventive concept.

Referring now to FIG. 26, the kernel applied 2404 (FIG. 24) may match the dimensionality of the data 2403 (FIG. 24) along 1 dimensional 2600; 1 dimensional+Time 2601; 2 dimensional 2602; 2 dimensional+Time 2603; 3 dimensional 2604; or 3 dimensional+Time 2605 spaces.

Figure 27:
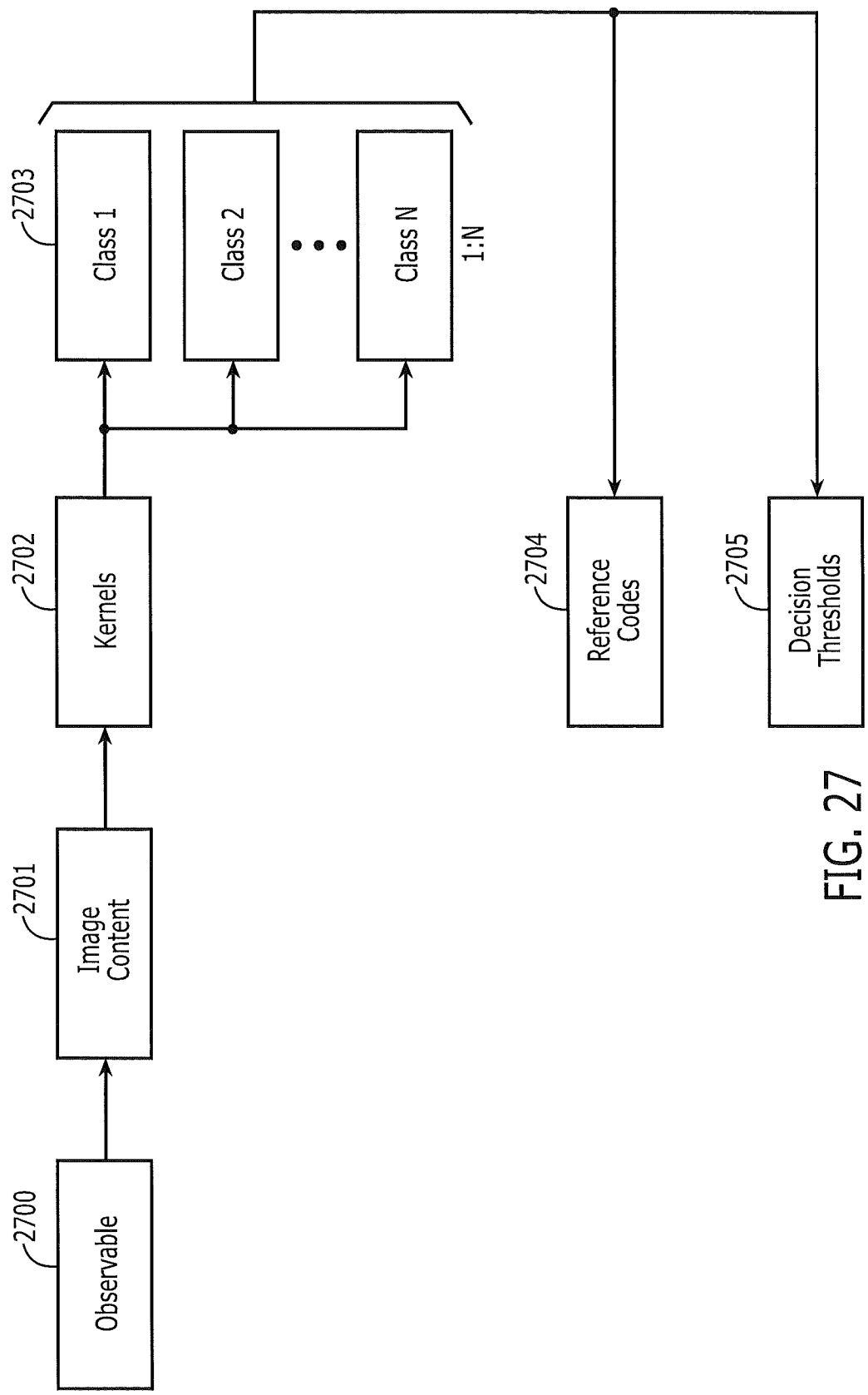
FIG. 27 is a block diagram illustrating generation of reference codes in accordance with some embodiments of the present inventive concept.

Referring now to FIG. 27, reference codes 2406 (FIG. 24) may be generated by acquiring data of the desired observable 2700 in the form of an image 2701 or other data set, and applying a kernel 2702 to extract feature classes of interest 2703, for example, Class 1, Class 2, Class N and the like. In some embodiments, kernels 2702 are optimized across many data sets to increase the likelihood that background variability between data sets containing the feature of interest allows for a clear decision threshold when the feature is or is not present. Once the kernels 2702 have been created, reference codes 2704 for each feature class 2703 may be created along with a decision threshold 2705 plot to indicate how close an input code 2405 (FIG. 24) must be to the class reference code to be included within the class (positive result) or excluded from the class (negative result). These kernels can be applied 2404 (FIG. 24) to the input data 2403 (FIG. 24) and compared against the reference codes generated 2704 to determine whether or not the feature class exists within the input data 2403 (FIG. 24).

As used herein, the "observable" 2700 may be a measured or derived parameter that may include, for example, spectra, structure, phase, flow, polarization, scattering coefficient or cross-section, anisotropy, or other biologically relevant optical parameters.

Kernels used 2702 may be class-specific and optimized to extract information content from the input data 2701 that is more likely to exist within a specific class 2703 and will select a specific class with high confidence. Other kernels 2702 may be more generic and targeted at determining class membership in one or more classes with lower confidence. For example, kernel 1 may be configured to target a specific feature within the input data and determines whether or not the input data contains that feature, while kernel 2 may be configured to loosely target multiple features within the input data to determine whether or not the input data may belong to a collection of classes.

A more detailed example will now be discussed. For example, kernel 1 may be configured to select for spatial frequencies that are indicative of tortuous vessels in diabetic retinopathy. Images with a low correlation with the "Human adult retina diabetic retinopathy tortuousity classifier" have a level or tortuosity (or lack of tortuosity) that indicates they may not have diabetic retinopathy. Kernel 2 may be configured to select for the general spatial frequency content and textural information associated with adult human retinal images. Images with a high correlation to the "Human adult retina general classifier" code are most likely human adult retina images.

As an extension, a family of filter kernels and classifier codes may be generated for disease states and run against the code generated from an input data set to determine if the data set may show some of the features indicative of one or more of the disease states. The same technique may be applied with a more general kernel family to determine in a broader sense an image classification such as, "adult human retina" or "adult human cornea."

Figure 28:
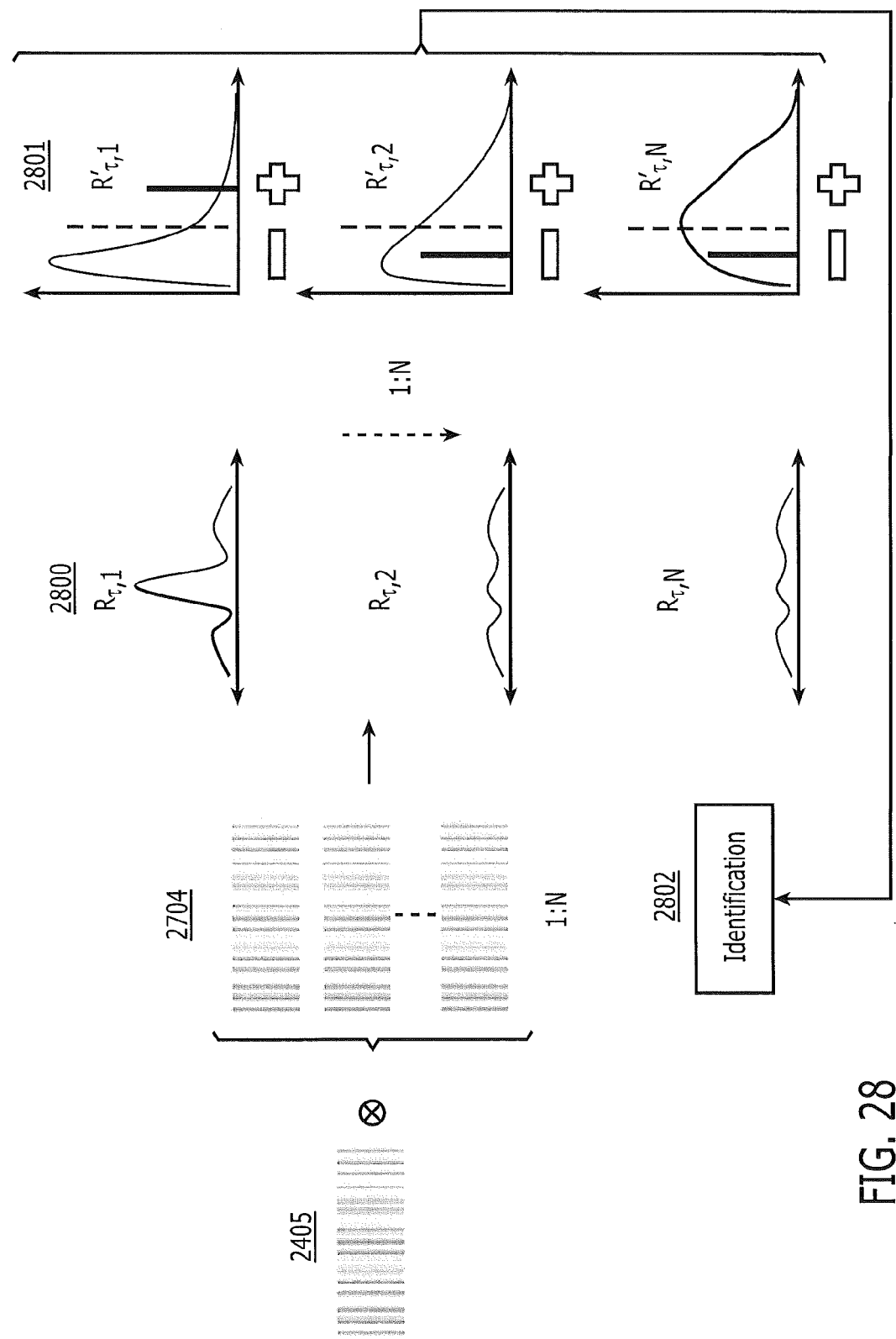
FIG. 28 is a diagram illustrating decision code processing and analysis in accordance with some embodiments of the present inventive concept.

Referring now to FIG. 28, the input code 2405 (FIG. 24) may be compared to a library of reference codes 2704 (FIG. 27) using, for example, cross-correlation or other integral or binary operation. The resultant function 2800, which may be a cross-correlation function, can be obtained for all codes in the reference library 2704 (FIG. 27) or all codes within a desired feature class. Each feature class may be linked with a decision curve 2801 as generated during the reference library creation process 2705 (Decision Thresholds—FIG. 27). If the peak of the resultant function 2800 lies within the positive decision region of only 1 code, then the input data 2403 (FIG. 24) may be deemed to contain features known to reside in the matched class 2802 (identification).

Figure 29:
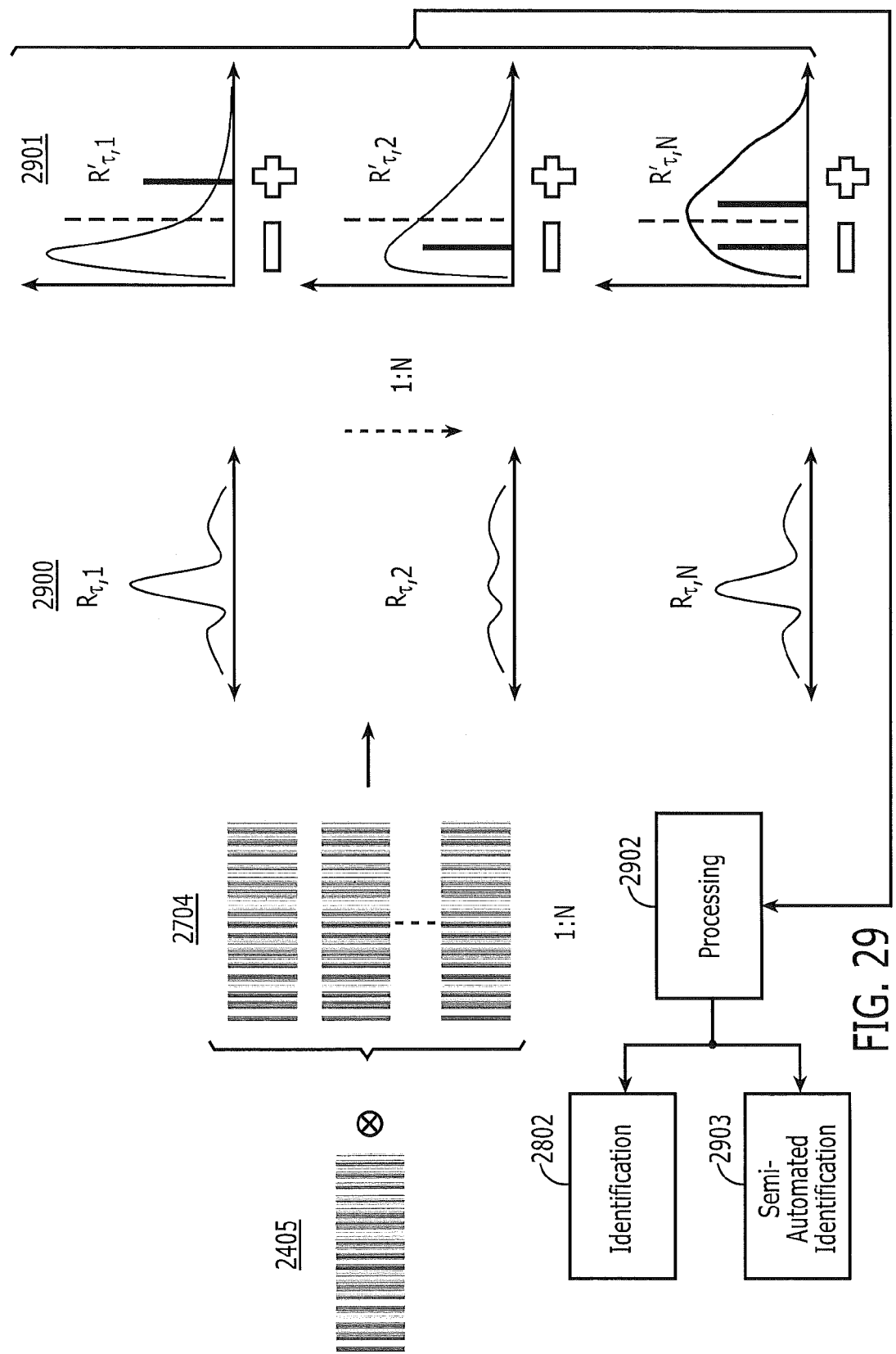
FIG. 29 a diagram illustrating decision code processing and analysis in accordance with some embodiments of the present inventive concept.

Referring now to FIG. 29, if the input code 2405 (FIG. 24) produces correlation (or other functional output) peaks 2900 that reside within the same region of the decision threshold of multiple codes 2901, then additional processing 2902 may be applied to determine which class is the closest fit for the code, flag the code as ambiguous or belonging to multiple classes, or return to the code generation phase 2404 (FIG. 24) with improved or modified kernel settings that may help in selection of a single class 2802 (FIG. 28). The confidence or relative relation to each of the reference codes may be reported to the user for semi-automated decision selection 2903.

Figure 30:
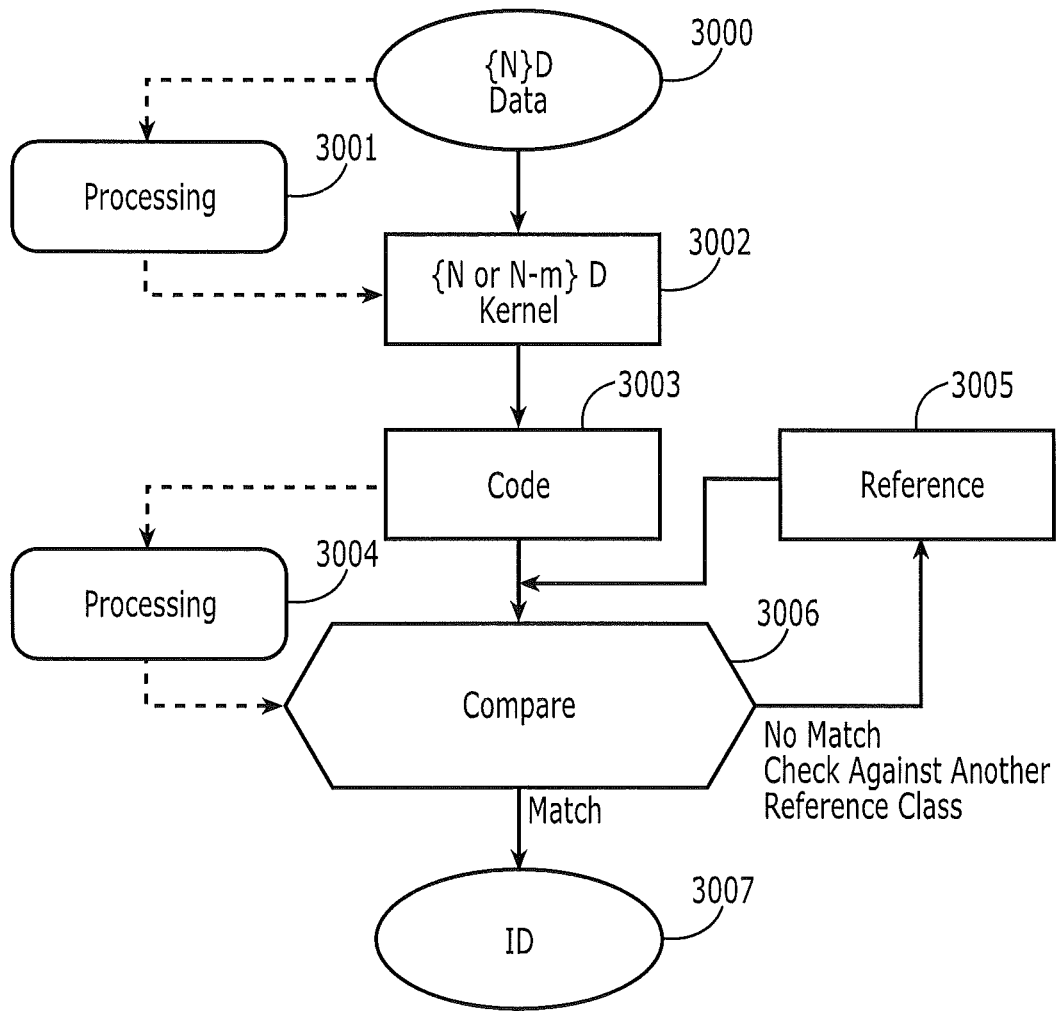
FIG. 30 is a flowchart illustrating processing steps in accordance with some embodiments of the present inventive concept.

Referring now to FIG. 30, N-Dimensional data 3000 may require additional processing 3001 before applying a generic or class-specific kernel 3002 to the N or N-m dimensional data. After a code is generated 3003, additional processing 3004 may be required before comparison 3006 with one or more reference codes 3005 before a decision or identification is made 3007.

Figure 31:
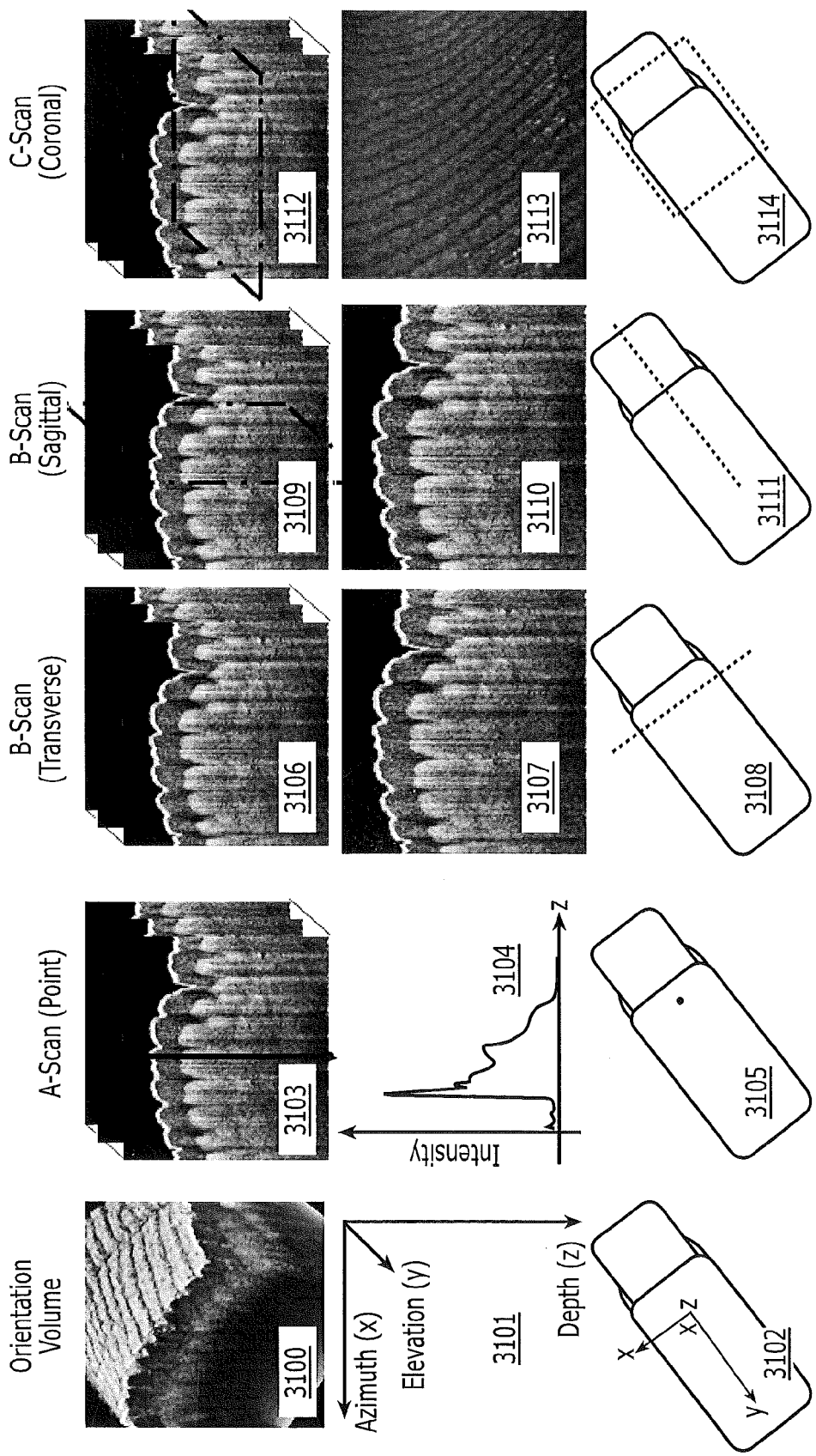
FIG. 31 are images and graphs illustrating slice planes through a 3D volume in the fingerprint according to some embodiments of the present inventive concept.

Referring now to FIG. 31, images and graphs illustrating slice planes through a 3D volume in the fingerprint according to some embodiments of the inventive concept will be discussed. Some embodiments of the present inventive concept involve the generation of a unique code from a 2-dimensional slice 3107 through a 3-dimensional volume 3100 acquired from the fingerprint. The orientation axes 3101 and corresponding fingerprint orientation 3102 are illustrated in FIG. 31. The traditional B-Scan consists of spatially unique locations along the azimuth dimension 3101 with a volume consisting of multiple B-Scans at spatially unique planes along the elevation dimension 3101. A single depth line 3103 (A-Scan) provides an intensity profile 3104 at a single, spatially unique scan position 3105. Transverse B-Scan slices 3106 provide images as a function of azimuth and depth 3107 through the fingerprint 3108. Sagittal slices through the structure 3109 provide similar B-Scan images 3110 through the fingerprint 3111. Once an FDOCT volume has been acquired, coronal slices 3112 and corresponding C-Scan images 3113 can be reconstructed for the fingerprint 3114. In some embodiments of the present inventive concept, a raster scan orthogonal to the banded structure in the fingerprint may be used. By acquiring multiple scans orthogonal to the bands in the fingerprint at different positions across the fingerprint, a volume of data 3100 is generated. Generating a projection along the depth axis returns a volume intensity projection. Some embodiments of the present inventive concept improve upon conventional methods by the addition of the depth dimension, which permits multiple methods of analysis.

Figure 32:
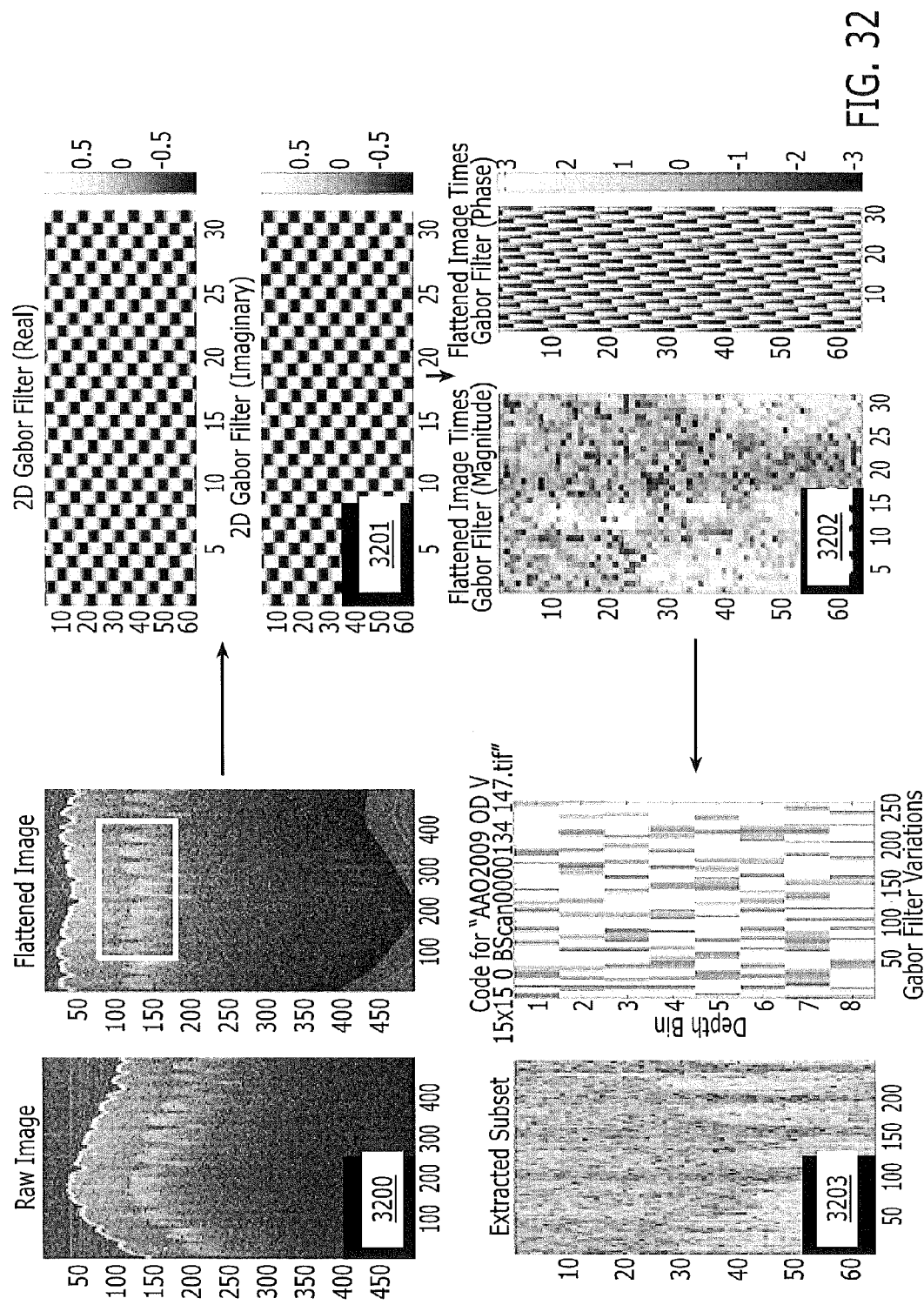
FIG. 32 is a diagram illustrating unique code generation from 1 slice plane through a 3D volume of fingerprint data according to some embodiments of the present inventive concept.

FIG. 32 illustrates the processing involved in the image analysis. The processing detailed above is applied to the extracted region, and a binary pair is generated for each set of filter values, yielding a map of bit values as illustrated in the code 3203 that is directly related to the unique spatial frequency content contained in each fingerprint's pattern.

In particular, diagrams of unique code generation from 1 slice through a 3D volume of fingerprint data according to some embodiments of the inventive concept will be discussed. In particular, methods of slicing data to best analyze the spatial frequency content of the tissue topology of the fingerprint will be discussed. Circular scans acquired of the fingerprint are flattened 3200 by finding the contour of the inner surface of fingerprint and warping the image based on the contour. A filter 3201 can then be applied to the data to extract or emphasize information content not readily available in the original image data. The fine structure can then be extracted from the fingerprint and processed 3202 to return a code 3203 unique to not only each individual but to each fingerprint as well.

Figure 33:
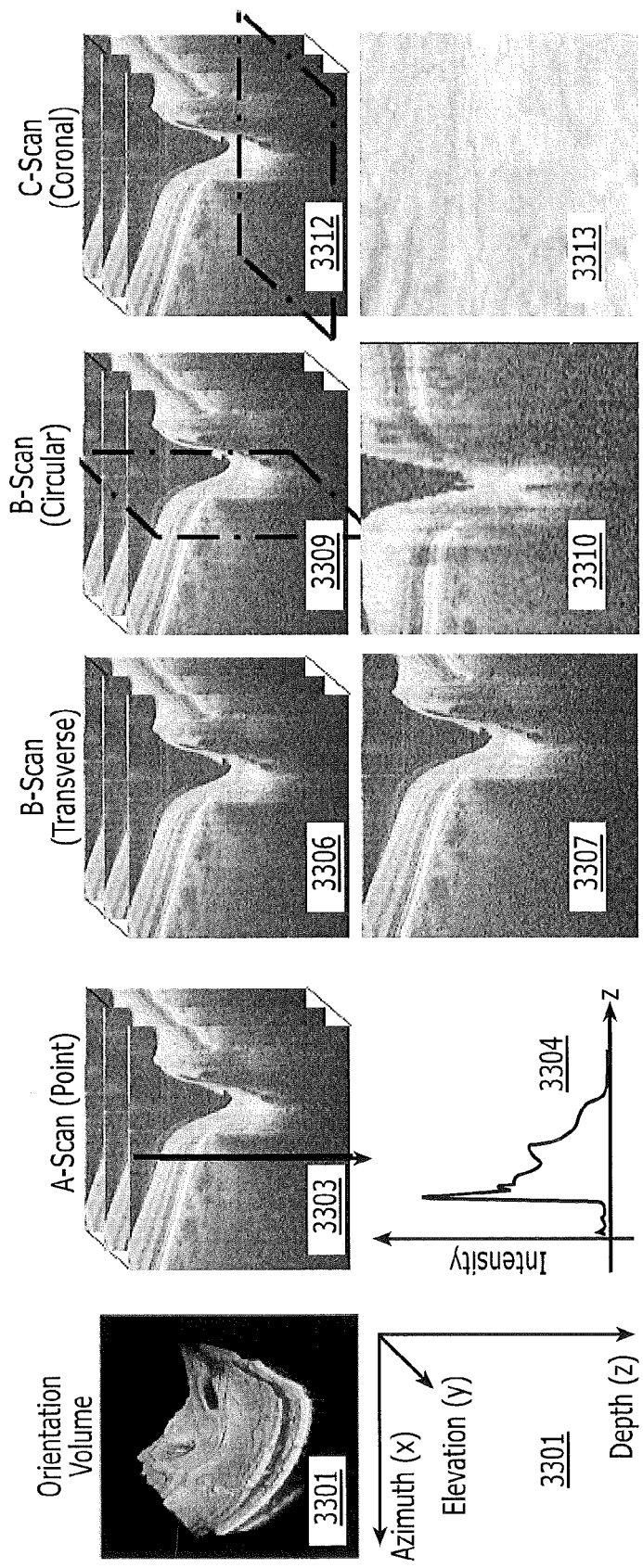
FIG. 33 are images and graphs illustrating slice planes through a 3D volume in the retina according to some embodiments of the present inventive concept.

Referring now to FIG. 33, images and graphs illustrating slice planes through a 3D volume in the retina according to some embodiments of the present inventive concept will be discussed. B-scans shown in FIG. 33 are examples meant to illustrate the approximate appearance of the data along each plane; the B-scan under the sagittal slice illustration is actually a transverse section. The image under the C-scan is actually a projection along the depth axis rather than an individual slice along the coronal plane.

As illustrated in FIG. 33, some embodiments of the present inventive concept involve the generation of a unique code from a 2-dimensional slice 3307 through a 3-dimensional volume 3300 acquired at the retina. The orientation axes 3301 and corresponding retina orientation 3302 are illustrated in FIG. 33. The traditional B-Scan consists of spatially unique locations along the azimuth dimension 3301 with a volume consisting of multiple B-Scans at spatially unique planes along the elevation dimension. A single depth line 3303 (A-Scan) provides an intensity profile 3304 at a single, spatially unique scan position 3305. Transverse B-Scan slices 3306 provide images as a function of azimuth and depth 3307 through the retina 3308. Sagittal slices through the structure 3309 provide similar B-Scan images 3310 through the retina 3311. Once an FDOCT volume has been acquired, coronal slices 3312 and corresponding C-Scan images 3313 can be reconstructed for the retina 3314. In some embodiments of the present inventive concept, a raster scan orthogonal to the banded structure in the retina may be used. By acquiring multiple scans orthogonal to the bands in the retina at different positions across the retina, a volume of data 3300 is generated. Generating a projection along the depth axis returns a volume intensity projection. Some embodiments of the present inventive concept improve upon conventional methods by the addition of the depth dimension, which permits multiple methods of analysis.

Figure 34:
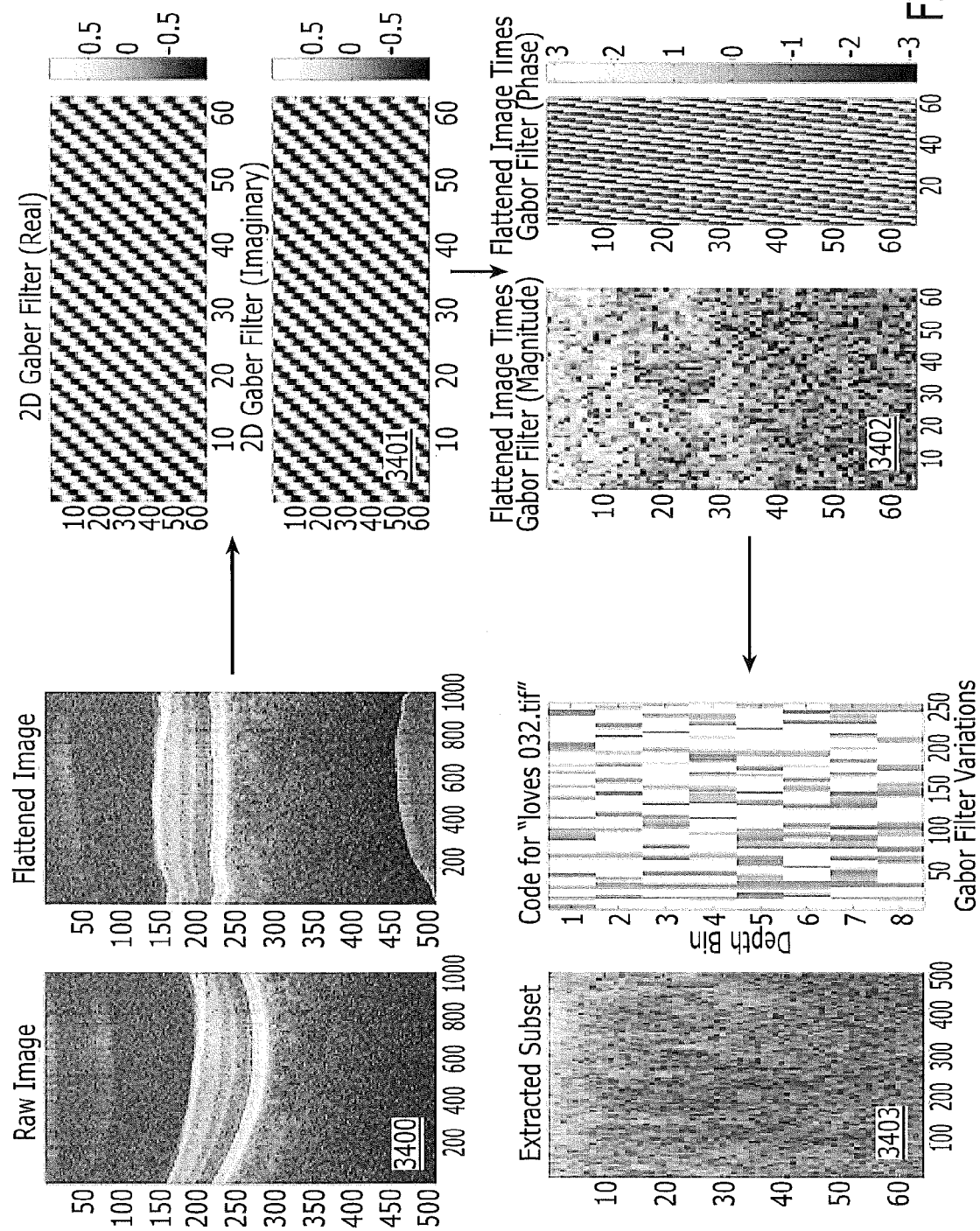
FIG. 34 is a diagram illustrating unique code generation from 1 slice plane through a 3D volume of retina data according to some embodiments of the present inventive concept.

FIG. 34 illustrates the processing involved in the image analysis. The processing detailed above is applied to the extracted region, and a binary pair is generated for each set of filter values, yielding a map of bit values as illustrated in the code 3403 that is directly related to the unique spatial frequency content contained in each retina's pattern. The choroidal region in FIG. 34 is selected and processed from a 2D frame of image data and the code generated from that image data.

Figure 35:
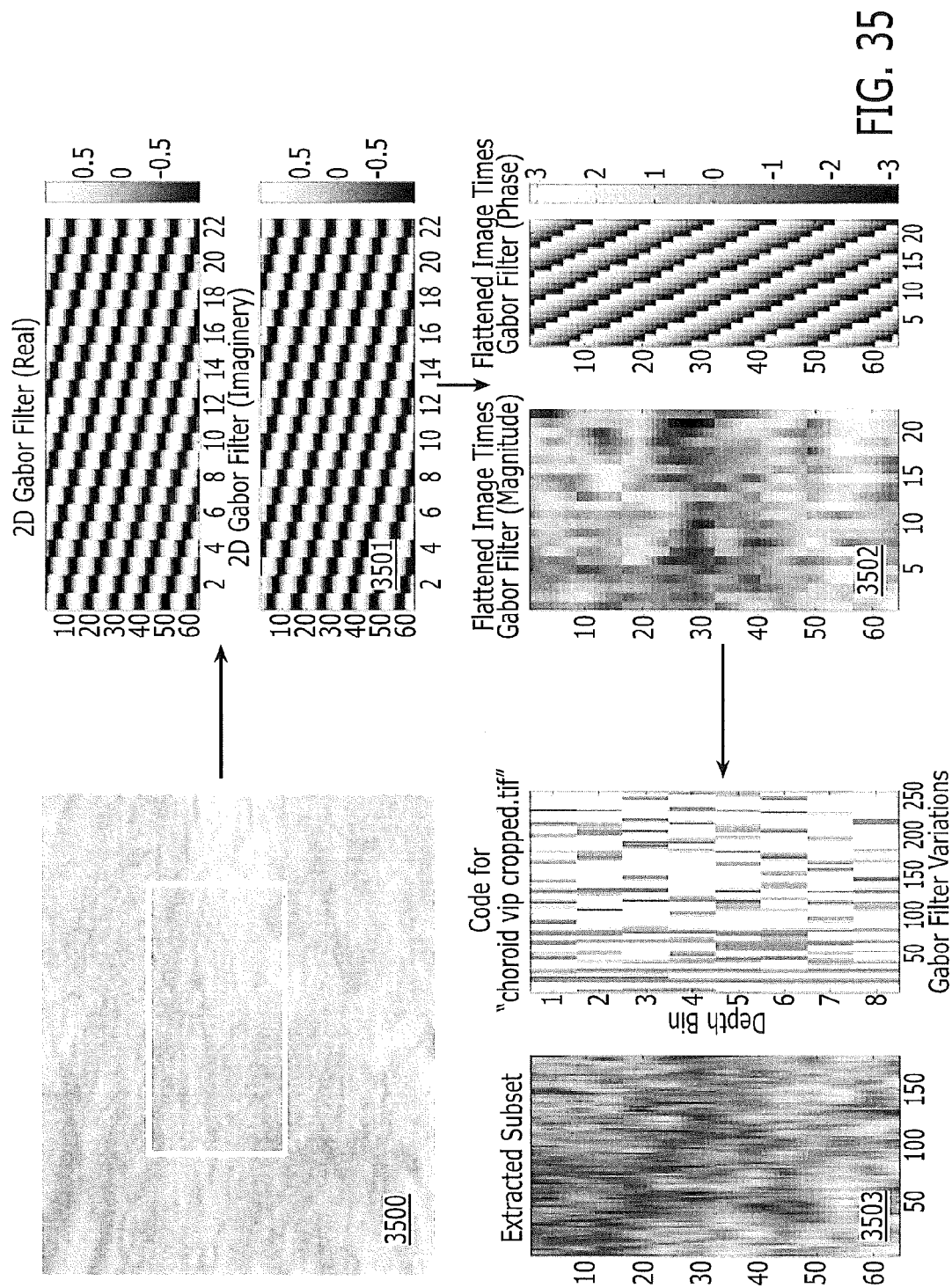
FIG. 35 is a diagram illustrating unique code generation from 1 slice plane through a 3D volume of retina data according to some embodiments of the present inventive concept.

In FIG. 35, the choroidal region is selected along a slice plane orthogonal to the depth axis, for example, horizontal line from every image in a volume was used to generate image 3500, from which the code is generated.

Figure 36:
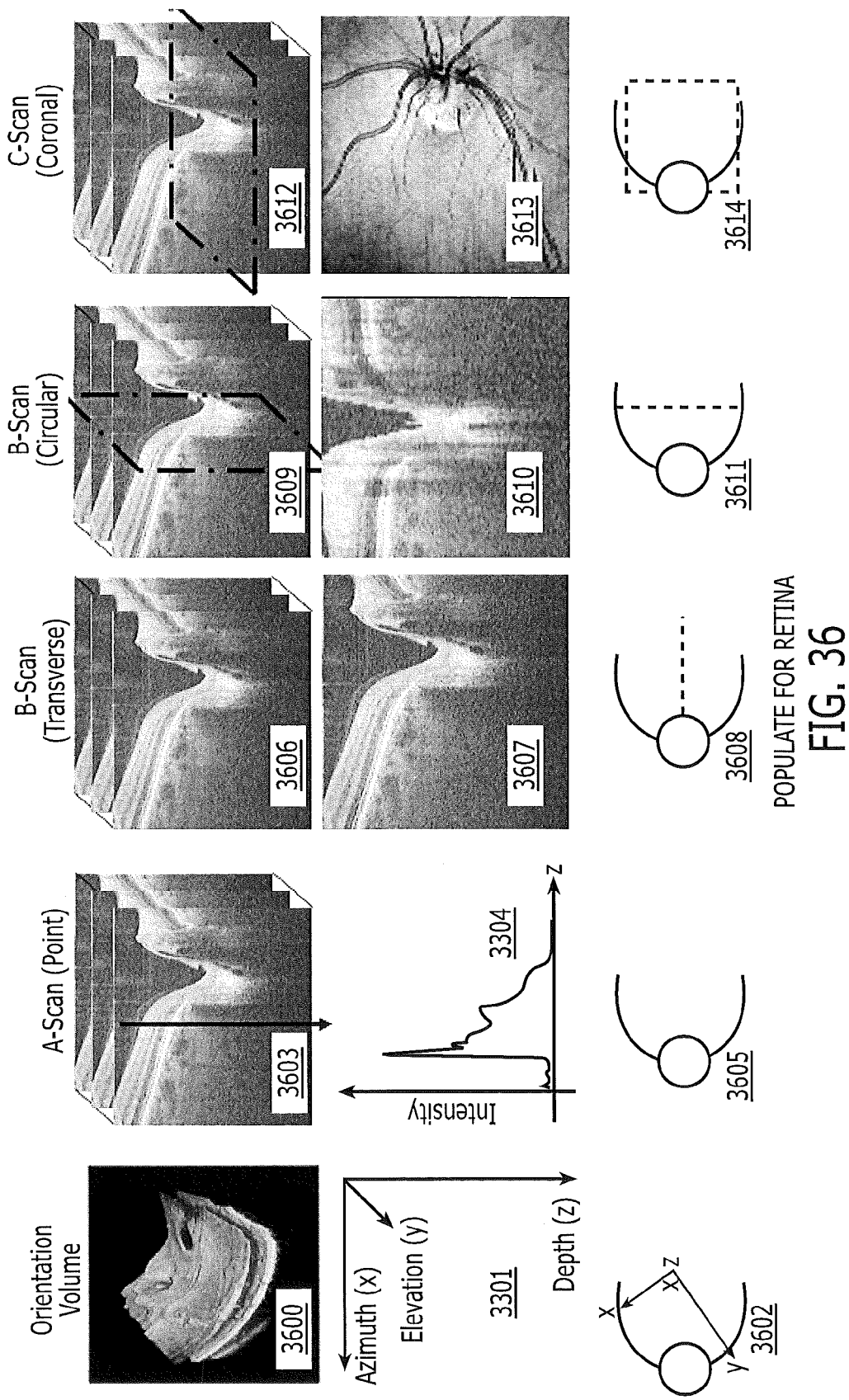
FIG. 36 is a diagram illustrating unique code generation from 1 slice plane through a 3D volume of retina vessels according to some embodiments of the present inventive concept.

Referring now to FIG. 36, images and graphs illustrating slice planes through a 3D volume in the retina according to some embodiments of the present inventive concept will be discussed. B-scans shown in FIG. 36 are examples meant to illustrate the approximate appearance of the data along each plane; the B-scan under the sagittal slice illustration is actually a transverse section. The image under the C-scan is actually a projection along the depth axis rather than an individual slice along the coronal plane.

As illustrated in FIG. 36, some embodiments of the present inventive concept involve the generation of a unique code from a 2-dimensional slice 3607 through a 3-dimensional volume 3600 acquired at the retina (vessels). The orientation axes 3601 and corresponding retina orientation 3602 are illustrated in FIG. 36. The traditional B-Scan consists of spatially unique locations along the azimuth dimension 3601 with a volume consisting of multiple B-Scans at spatially unique planes along the elevation dimension. A single depth line 3603 (A-Scan) provides an intensity profile 3604 at a single, spatially unique scan position 3605. Transverse B-Scan slices 3606 provide images as a function of azimuth and depth 3607 through the retina 3608. Sagittal slices through the structure 3609 provide similar B-Scan images 3610 through the retina 3611. Once an FDOCT volume has been acquired, coronal slices 3612 and corresponding C-Scan images 3613 can be reconstructed for the retina 3614. In some embodiments of the present inventive concept, a raster scan orthogonal to the banded structure in the retina may be used. By acquiring multiple scans orthogonal to the bands in the retina at different positions across the retina, a volume of data 3600 is generated. Generating a projection along the depth axis returns a volume intensity projection. Some embodiments of the present inventive concept improve upon conventional methods by the addition of the depth dimension, which permits multiple methods of analysis.

Figure 37:
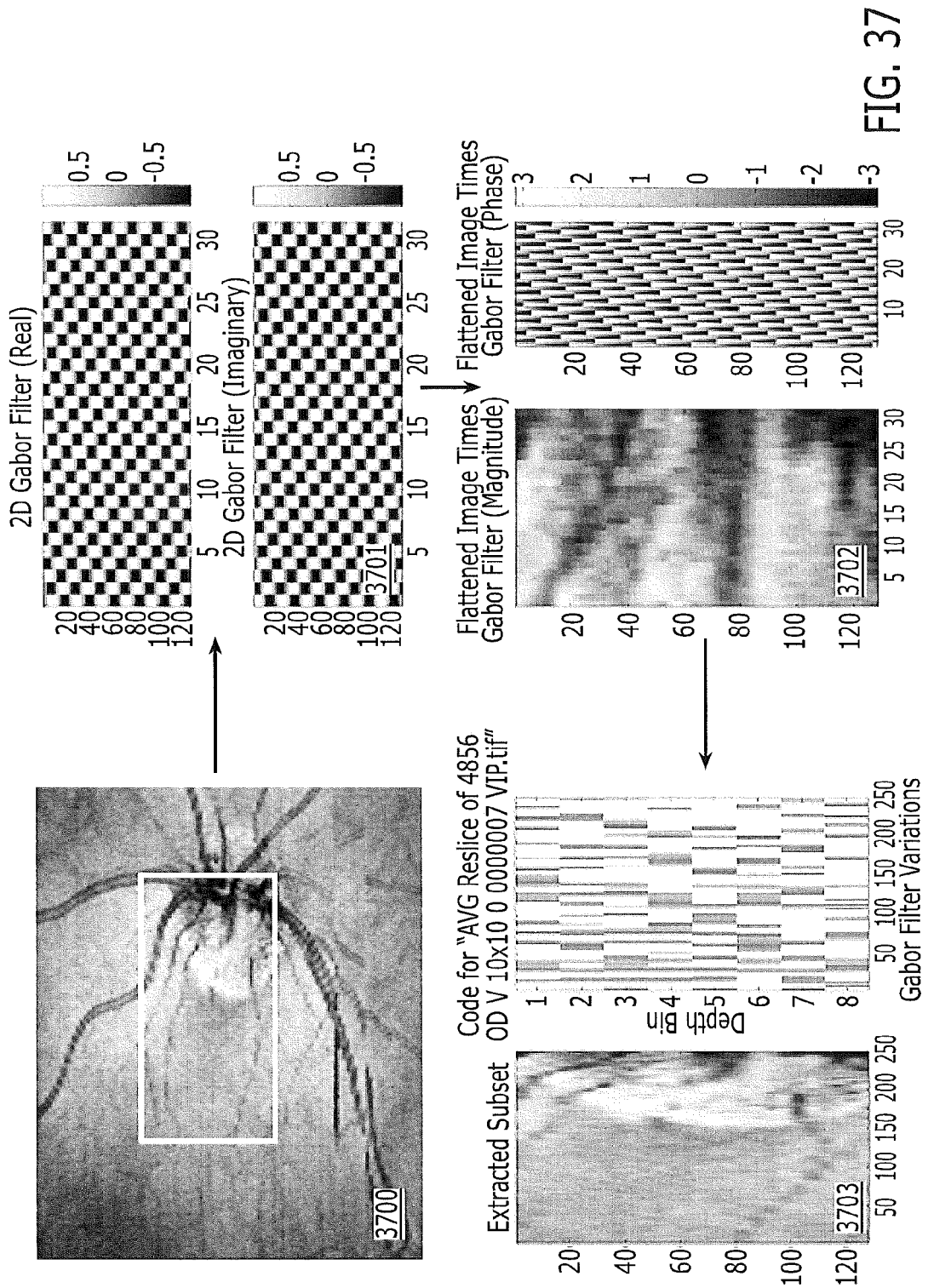
FIG. 37 are images and graphs illustrating slice planes through a 3D volume in the retina vessels according to some embodiments of the present inventive concept.

Referring now to FIG. 37, processing involved in the image analysis of the retina vessels will be discussed. The processing detailed above is applied to the extracted region, and a binary pair is generated for each set of filter values, yielding a map of bit values as illustrated in the code 3703 that is directly related to the unique spatial frequency content contained in each retina's pattern.

In the drawings and specification, there have been disclosed exemplary embodiments of the inventive concept. However, many variations and modifications can be made to these embodiments without substantially departing from the principles of the present inventive concept. Accordingly, although specific terms are used, they are used in a generic and descriptive sense only and not for purposes of limitation, the scope of the inventive concept being defined by the following claims.

That which is claimed is:

1. A method of providing a diagnosis using a digital code associated with an image, the method comprising:
    collecting a multidimensional image of a subject, the multidimensional image having at least two dimensions;
    extracting a two dimensional subset of the multidimensional image;
    reducing the multidimensional image to a first code that is unique to the multidimensional image of the subject based on the extracted two dimensional image;
    comparing the first unique code associated with the subject to a library of reference codes, each of the reference codes in the library of reference codes being indicative of a class of objects;
    determining if the subject associated with the first unique code falls into at least one of the classes of objects associated with the reference codes based on a result of the comparison; and
    formulating a diagnostic decision based on the whether the first unique code associated with the subject falls into at least one of the classes associated with the reference code,
    wherein determining if the subject associated with the first unique reference code falls into at least one of the classes further includes determining if the subject associated with the first unique reference code has changed classes over time; and
    wherein formulating the diagnostic decision comprises formulating the diagnostic decision based on the change of class over time.

2. The method of claim 1, wherein determining if the subject associated with the first unique code falls into at least one of the classes of objects comprises determining that the subject associated with the first unique code falls into at least two of the classes, the method further comprising:
    applying additional processing to determine which of the at least two classes more accurately identifies the subject associated with the first unique code.

3. The method of claim 1, wherein the classes associated with the reference code identify at least one of a physical state and a physical object.

4. The method of claim 3, wherein the subject comprises at least one of a fingernail bed, a fingerprint, an iris, a cornea, a retina, retinal vessels, any human tissue and physical object.

5. The method of claim 1, wherein reducing further comprises reducing the two dimensional subset to the first unique code based on a defined set of structural or functional information contained with the image, the method further comprising:
    storing the first unique code; and
    comparing the first unique code to a second unique code to establish a degree of equivalence of the first and second codes.

6. The method of claim 1, wherein the multidimensional image comprises at least one of a volumetric image representative of one of structural and functional information in a sample.

7. The method of claim 5, where reducing the two dimensional subset to the first unique code comprises:
    manipulating the multidimensional data to extract a region of interest;

extracting the structural or the functional information using a filter;

translating the filtered information into the first unique code representative of the information content contained in the multidimensional data;

manipulating the first unique code to be compared to other codes; and comparing two or more codes to assess a degree of equivalents between the codes.

8. The method of claim 7, wherein extracting comprises extracting using a filter configured to extract the structural or functional information.

9. The method of claim 8, wherein the filter comprises at least one of a Gabor filter, a complex filter that consists of real and imaginary parts, a complex filter that consists of a spatial frequency component and a Gaussian window component and a complex filter that has at least three unique degrees of freedom including amplitude, at least one spatial frequency, and at least one Gaussian window standard deviation.

10. The method of claim 8, wherein the filter is configured to operate on a two dimensional subset using at least one of a convolution in the native domain or a multiplication of the Fourier Transforms of the filter and two dimensional subset and multiple filter scales in which one or more filter degrees of freedom are changed before combination with the image subset.

11. The method of claim 8, wherein the unique code is obtained from complex data comprising at least one of a complex representation of the filter combined with the image subset in which the complex result is treated as a vector in the complex plane and a method in which the angle of the vector in the complex plane is determined and a code representative of the quadrant in the complex plane containing the vector angle is generated.

12. The method of claim 1, wherein the unique code is binary such that each pixel of information is represented by one of two states.

13. The method of claim 1, wherein the unique code has a base greater than 2.

14. The method of claim 1, wherein the unique code is represented as a one or two dimensional barcode configured to be read by a generic commercial barcode reading technology.

15. The method of claim 5, wherein comparing comprises comparing two or more unique codes using cross-correlation or other relational comparison.

16. The method of claim 15, wherein the relational comparison comprises an XOR operation.

17. The method of claim 15, wherein the comparison result is applied to find a Hamming distance.

18. The method of claim 17, wherein the Hamming distance is used to validate a strength of the comparison against a database of other codes.

19. The method of claim 7, further comprising:
repeating extracting, translating, manipulating, comparing and assigning to construct a database of codes; and
defining a unique identifier threshold based on sensitivity analysis of the codes in the database.

20. The method of claim 19, further comprising determining if a calculated code is unique or present in the database by comparing the unique identifier threshold to the Hamming distance between the calculated code and the codes in the database.

21. The method of claim 8, wherein the filter comprises any image processing system in which information content is emphasized or extracted from a depth-dependent image.

22. The method of claim 21, wherein the filter comprises at least one of a speckle tracking algorithm and a texture-based image analysis algorithm.

23. The method of claim 1, wherein the method is performed using an optical coherence tomography (OCT) imaging system.

24. A computer program of providing a digital code associated with an image, the computer program product comprising a non-transitory computer readable storage medium having computer readable program code embodied in said medium, the computer readable program code comprising program code configured to carry out the method of claim 1.

25. A method for providing a diagnosis using a digital code in an optical coherence tomography imaging system, the method comprising:
acquiring interferometric cross-correlation data representative of multidimensional information unique to a sample, the multidimensional information including one, two, or three spatial dimensions plus no greater than two time dimensions;
processing the multidimensional interferometric cross-correlation data into one or more images processed to represent one of structural and functional information about the sample;
selecting a subset of the multidimensional data;
reducing the selected subset of data to a two dimensional subset of data;
performing one or more spatial or temporal frequency transforms of the two dimensional subsets to derive a unique representation of the sample;
reducing the transform into a unique digital code associated with the sample;
comparing the unique digital code associated with the sample to a library of reference codes, each of the reference codes in the library of reference codes being indicative of a class of objects;
determining if the sample associated with the unique digital code falls into at least one of the classes of objects associated with the reference codes based on a result of the comparison; and
formulating a diagnostic decision based on the whether the unique digital code associated with the sample falls into at least one of the classes associated with the reference code.

26. The method of claim 25, wherein the optical coherence tomography system comprises:
an optical source;
an optical splitter configured to separate a reference optical signal from a sample optical signal; and
an optical detector configured to detect an interferometric cross-correlation between the reference optical signal and the sample optical signal.

27. The method of claim 26, wherein the unique digital code comprises a first unique digital code, the method further comprising:
storing the digital code;
comparing the first unique digital code to a second unique digital code of the sample acquired from a second position within the sample, of the same sample acquired at a different time and/or of a different sample; and
establishing a degree of equivalence between the first and second unique digital codes.

28. The method of claim 25, wherein the method is performed using an optical coherence tomography (OCT) imaging system.

29. A computer program of providing a digital code associated with an image, the computer program product comprising a non-transitory computer readable storage medium having computer readable program code embodied in said medium, the computer readable program code comprising program code configured to carry out the method of claim 25.

30. A method of providing a diagnosis using a digital code using a Fourier domain optical coherence tomography imaging system, the method comprising:
acquiring frequency-dependent interferometric cross-correlation data representative of multidimensional information unique to a sample, the multidimensional information including no greater than one frequency dimensions, one, two, or three spatial dimensions and no greater than two time dimensions;
processing the multidimensional interferometric cross-correlation data into one or more images processed to represent one of structural and functional information about the sample; and
selecting a subset of the multidimensional data;
reducing the subset of data to a two dimensional subset of data;
performing one or more spatial or temporal frequency transforms of the two dimensional subsets to derive a unique representation of the sample;
reducing the transform into a unique digital code that provides a unique signature of the multidimensional data;
comparing the unique digital code associated with the sample to a library of reference codes, each of the reference codes in the library of reference codes being indicative of a class of objects;
determining if the sample associated with the unique digital code falls into at least one of the classes of objects associated with the reference codes based on a result of the comparison; and
formulating a diagnostic decision based on the whether the unique digital code associated with the sample falls into at least one of the classes associated with the reference code.

31. The method of claim 30, wherein the Fourier domain optical coherence tomography imaging system comprises:
an optical source;
an optical splitter configured to separate a reference optical signal from a sample optical signal; and
an optical detector configured to detect a frequency-dependent interferometric cross-correlation between the reference signal and the sample signal.

32. The method of claim 31, wherein the unique digital code comprises a first unique digital code, the method further comprising:
storing the unique digital code;
comparing the unique digital code to a second unique digital code of the same sample acquired from a separate position within the sample, of the sample acquired at a separate time, of a different sample; and
establishing a degree of equivalence between the first and second unique digital codes.

33. The method of claim 32, wherein processing of frequency-dependent interferometric cross-correlation data comprises obtaining a Fourier transformation of the frequency-dependent dimension to provide a spatial dimension.

34. The method of claim 30:
wherein the image is a volumetric image of a fingernail of a subject;
wherein the volumetric image includes a series of one-dimensional lines that provide information on scattering from the fingernail and fingernail bed as a function of depth;
wherein a series of lines optically contiguous are arrayed in a two-dimensional frame that represents a cross section of the fingernail perpendicular to an axis of the finger, and
wherein the method further comprises acquiring a series of frames to produce a volume.

35. The method of claim 34, further comprising:
segmenting a nailbed from within the volumetric image of the fingernail using an automated or manual segmentation technique; and
averaging one or more frames in order to produce an average-valued image of multiple cross-sectional locations of the nailbed or to improve the signal-to-noise ratio of the nailbed image along one cross-section.

36. The method of claim 35, further comprising processing a digital code from the cross-sectional image of segmented nailbed region of at least one frame.

37. The method of claim 36, wherein processing the multidimensional interferometric cross-correlation data comprises processing an intensity projection from two or more frames of the segmented nailbed, the method further comprising processing a digital code from the intensity projection.

38. The method of claim 30, wherein the image is a volumetric image of an iris of an eye of a subject, wherein the volumetric image includes a series of one-dimensional lines that provide information on scattering from the iris as a function of depth, wherein a series of lines optically contiguous are arrayed in a two-dimensional frame that represents a cross section of the iris perpendicular to an axis of the eye, the method further comprising acquiring a series of frames to produce a volume.

39. The method of claim 38, further comprising constructing the volumetric image from a series of concentric circular scans approximately centered on a pupil of the eye.

40. The method of claim 38, further comprising:
segmenting one or more layers of the iris from within the volumetric image of the iris using an automated or manual segmentation technique; and
averaging one or more frames in order to produce an average-valued image of multiple cross-sectional locations of the iris or to improve the signal-to-noise ratio of the iris image at cross section.

41. The method of claim 40, further comprising processing a digital code from the cross-sectional image of segmented iris region of at least one frame.

42. The method of claim 38, further comprising:
processing an intensity projection from two or more frames of the segmented iris; and
processing a digital code from the intensity projection.

43. The method of claim 30, wherein the method is performed using an optical coherence tomography (OCT) imaging system.

44. A computer program of providing a digital code associated with an image, the computer program product comprising a non-transitory computer readable storage medium having computer readable program code embodied in said medium, the computer readable program code comprising program code configured to carry out the method of claim 30.

45. An optical coherence tomography imaging system comprising:
means for acquiring interferometric cross-correlation data representative of multidimensional information unique to a sample, the multidimensional information including one, two, or three spatial dimensions plus no greater than two time dimensions;
means for processing the multidimensional interferometric cross-correlation data into one or more images processed to represent one of structural and functional information about the sample; and means for selecting a subset of the multidimensional data;

means for reducing the selected subset of data to a two dimensional subset of data;

means for performing one or more spatial or temporal frequency transforms of the two dimensional subsets to derive a unique representation of the sample;

means for reducing the transform into a unique digital code associated with the sample;

means for comparing the unique digital code associated with the sample to a library of reference codes, each of the reference codes in the library of reference codes being indicative of a class of objects;

means for determining if the sample associated with the unique digital code falls into at least one of the classes of objects associated with the reference codes based on a result of the comparison; and means for formulating a diagnostic decision based on the whether the unique digital code associated with the sample falls into at least one of the classes associated with the reference code.

46. The system of claim 45, further comprising:

an optical source;

an optical splitter configured to separate a reference optical signal from a sample optical signal; and an optical detector configured to detect an interferometric cross-correlation between the reference optical signal and the sample optical signal.

47. The system of claim 46, wherein the unique digital code comprises a first unique digital code, the system further comprising:

means for storing the digital code;

means for comparing the first unique digital code to a second unique digital code of the sample acquired from a second position within the sample, of the same sample acquired at a different time and/or of a different sample; and means for establishing a degree of equivalence between the first and second unique digital codes.

48. A Fourier domain optical coherence tomography imaging system comprising:

means for acquiring frequency-dependent interferometric cross-correlation data representative of multidimensional information unique to a sample, the multidimensional information including no greater than one frequency dimensions, one, two, or three spatial dimensions and no greater than two time dimensions;

means for processing the multidimensional interferometric cross-correlation data into one or more images processed to represent one of structural and functional information about the sample;

means for selecting a subset of the multidimensional data;

means for reducing the subset of data to a two dimensional subset of data;

means for performing one or more spatial or temporal frequency transforms of the two dimensional subsets to derive a unique representation of the sample;

means for reducing the transform into a unique digital code that provides a unique signature of the multidimensional data;

means for comparing the unique digital code associated with the sample to a library of reference codes, each of the reference codes in the library of reference codes being indicative of a class of objects;

means for determining if the sample associated with the unique digital code falls into at least one of the classes of objects associated with the reference codes based on a result of the comparison; and means for formulating a diagnostic decision based on the whether the unique digital code associated with the sample falls into at least one of the classes associated with the reference code.

49. The system of claim 48, further comprising:

an optical source;

an optical splitter configured to separate a reference optical signal from a sample optical signal; and an optical detector configured to detect a frequency-dependent interferometric cross-correlation between the reference signal and the sample signal.

50. The system of claim 48, wherein the unique digital code comprises a first unique digital code, the system further comprising:

means for storing the unique digital code;

means for comparing the unique digital code to a second unique digital code of the same sample acquired from a separate position within the sample, of the sample acquired at a separate time, of a different sample; and a means for establishing a degree of equivalence between the first and second unique digital codes.

* * * * *